US008507018B2

(12) United States Patent
Chevaux et al.

(10) Patent No.: US 8,507,018 B2
(45) Date of Patent: Aug. 13, 2013

(54) PRODUCTS CONTAINING POLYPHENOL(S) AND L-ARGININE AND METHODS OF USE THEREOF

(75) Inventors: Kati A. Chevaux, Mount Arlington, NJ (US); Harold H. Schmitz, Bethesda, MD (US); Leo J. Romanczyk, Hackettstown, NJ (US)

(73) Assignee: Mars, Incorporated, McLean, VA (US)

( * ) Notice: Subject to any disclaimer, the term of this patent is extended or adjusted under 35 U.S.C. 154(b) by 1145 days.

(21) Appl. No.: 10/790,289

(22) Filed: Mar. 1, 2004

(65) Prior Publication Data

US 2004/0166142 A1 Aug. 26, 2004

Related U.S. Application Data

(60) Division of application No. 10/176,126, filed on Jun. 19, 2002, now Pat. No. 6,805,883, which is a continuation of application No. 09/284,783, filed as application No. PCT/US99/05545 on Mar. 12, 1999, now abandoned, which is a continuation-in-part of application No. 09/041,327, filed on Mar. 12, 1998, now abandoned.

(51) Int. Cl.
*A61K 36/00* (2006.01)

(52) U.S. Cl.
USPC ............ 424/776; 424/725; 424/400; 424/439

(58) Field of Classification Search
USPC .................................................. 424/439, 776
See application file for complete search history.

(56) References Cited

U.S. PATENT DOCUMENTS

| | | | |
|---|---|---|---|
| 3,769,030 A | 10/1973 | Kleinert | |
| 4,208,440 A | 6/1980 | Schmidt | |
| 4,364,967 A | 12/1982 | Black | |
| 4,421,771 A | 12/1983 | Stock et al. | |
| 4,619,831 A | 10/1986 | Sharma | |
| 4,704,292 A | 11/1987 | Kattenberg | |
| 4,797,421 A | 1/1989 | Ariga et al. | |
| 4,871,557 A | 10/1989 | Linscott | |
| 4,948,600 A | 8/1990 | Zumbe et al. | |
| 5,217,997 A | 6/1993 | Levere et al. | |
| 5,362,505 A | 11/1994 | Hsieh et al. | |
| 5,428,070 A | 6/1995 | Cooke et al. | |
| 5,431,912 A | 7/1995 | N Guyen | |
| 5,484,594 A | 1/1996 | Frangi et al. | |
| 5,520,950 A | 5/1996 | Rosenplenter | |
| 5,543,430 A | 8/1996 | Kaesemeyer | |
| 5,554,645 A * | 9/1996 | Romanczyk et al. | 514/453 |
| 5,585,135 A | 12/1996 | Patterson et al. | |
| 5,820,910 A | 10/1998 | Jury et al. | |
| 5,891,905 A * | 4/1999 | Romanczyk et al. | 514/449 |
| 5,922,756 A * | 7/1999 | Chan | 514/456 |
| 5,945,452 A * | 8/1999 | Cooke et al. | 514/564 |
| 6,013,632 A * | 1/2000 | Jones et al. | 514/3.7 |
| 6,015,913 A | 1/2000 | Kealey et al. | |
| 6,063,432 A | 5/2000 | Maxwell et al. | |
| 6,107,281 A * | 8/2000 | Jones et al. | 514/3.7 |
| 6,127,421 A * | 10/2000 | Wideman et al. | 514/565 |
| 6,297,273 B1 * | 10/2001 | Romanczyk, Jr. | 514/456 |
| 6,423,743 B1 * | 7/2002 | Romancyzk, Jr. | 514/456 |
| 6,469,053 B1 | 10/2002 | Romanczyk et al. | |
| 6,610,320 B2 * | 8/2003 | Schmitz et al. | 424/440 |
| 6,638,971 B2 * | 10/2003 | Romanczyk et al. | 514/456 |
| 6,670,390 B1 * | 12/2003 | Romanczyk et al. | 514/456 |
| 6,747,059 B1 * | 6/2004 | Romanczyk et al. | 514/456 |
| 6,805,883 B2 * | 10/2004 | Chevaux et al. | 424/725 |
| 6,900,241 B2 * | 5/2005 | Romanczyk et al. | 514/456 |
| 6,998,417 B2 * | 2/2006 | Romanczyk et al. | 514/456 |
| 7,115,656 B2 * | 10/2006 | Romanczyk et al. | 514/456 |
| 7,122,574 B2 * | 10/2006 | Romanczyk et al. | 514/456 |
| 7,723,379 B2 * | 5/2010 | Romanczyk et al. | 514/456 |
| 7,754,760 B2 * | 7/2010 | Romanczyk et al. | 514/456 |
| 7,868,042 B2 * | 1/2011 | Romanczyk et al. | 514/456 |
| 7,875,651 B2 * | 1/2011 | Romanczyk et al. | 514/456 |
| 8,377,424 B2 * | 2/2013 | Romanczyk et al. | 424/58 |
| 2002/0018807 A1 * | 2/2002 | Schmitz et al. | 424/450 |
| 2003/0104075 A1 * | 6/2003 | Chevaux et al. | 424/725 |
| 2003/0180406 A1 * | 9/2003 | Sies | 424/776 |
| 2004/0081715 A1 * | 4/2004 | Schmitz et al. | 424/776 |
| 2004/0166142 A1 * | 8/2004 | Chevaux et al. | 424/439 |
| 2011/0268846 A1 * | 11/2011 | Nair et al. | 426/73 |

FOREIGN PATENT DOCUMENTS

| | | | |
|---|---|---|---|
| FR | 2 384 461 A | | 10/1978 |
| FR | 2 725 113 A | | 4/1996 |

(Continued)

OTHER PUBLICATIONS

Derwent 1997-525196, Aug. 1997, Derwent or SE 9, Faendriks.*
Klahr, S., The Role of L-Arginine in Hypertension and Nephrotoxicity, *Current Opinions in Nephrology and Hypertension*, 7:547-550(1998).
Sabate et al., *Effects of Walnuts on Serum Lipid Levels and Blood Pressure in Normal Men*, New England Journal of Medicine 1993, 328:603-607.
Sabate et al., *Nuts: A New Protective Food Against Coronary Heart Disease*, Current Opinion in Lipidology, 1994, 5:11-16.
Rossitch, Jr., *L-Arginine Normalizes Endothelial Function in Cerebral Vessels from Hypercholesterolemic Rabbits*, J. Clin. Invest., 1991, 87:1295-1299.

(Continued)

*Primary Examiner* — Chris R Tate
(74) *Attorney, Agent, or Firm* — Nath, Goldberg & Meyer; Lakshmi Rajan; Sheldon M. McGee

(57) ABSTRACT

Foods and pharmaceuticals which contain cocoa and/or nut procyanidin(s) in combination with L-arginine are effective to induce a physiological increase in nitric oxide production in a mammal having ingested the product. A preferred food product is a confection, particularly a dark or milk chocolate containing nuts. The procyanidins may be natural or synthetic and may be provided by food ingredients such as chocolate liquor and/or cocoa solids prepared from underfermented beans and nut skins. The L-arginine may be natural or synthetic and may be provided by food ingredients such as nut meats, nut pastes, and/or nut flours, seeds, seed pastes, and/or seed flours, or gelatin. The beneficial health effects may include, for example, reduced blood pressure, resistance to cardiovascular disease, and anticancer activity.

26 Claims, No Drawings

(56) References Cited

FOREIGN PATENT DOCUMENTS

| JP | 60049751 A2 | 3/1985 |
|---|---|---|
| JP | 7 213251 A | 8/1995 |
| JP | 8 205818 | 8/1996 |
| RO | 76074 | 1/1982 |
| WO | 97 36497 A | 10/1997 |
| WO | 98/09533 | 3/1998 |
| WO | 98 33494 A | 8/1998 |

OTHER PUBLICATIONS

*Arginine: No More Than a Simple Amino Acid?*, The Lancet, 1997, 350:901-902.

Girerd et al., *L-Arginine Augments Endothelium-Dependent Vasodilation in Cholesterol-Fed Rabbits*, Circulation Research, 1990, 67:6 1301-1308.

Drexler et al., *Correction of Endothelial Dysfunction in Coronary Miscrocirculation of Hypercholesterolaemic Patients by L-Arginine*, The Lancet, 1991, 338:1546-1550.

Creager et al., *L-Arginine Improves Endothelium-Dependent Vasodilation in Hypercholesterolemic Humans*, J. Clin. Invest., 1992, 90:1248-1253.

Cooke et al., *Arginine Restores Cholinergic Relaxation of Hypercholesterolemic Rabbit Thoracic Aorta*, Circulation, 1991, 83:3 1057-1062.

Cooke et al., *Anti-Atherogenic Effect of Nuts: Is the Answer No?*, Arch Intern Med, 1993, 153-896-899.

Clarkson, et al., *Oral L-Arginine Improves Endothelium-Dependent Dilation in Hypercholesterolemic Young Adults*, J. Clin. Invest., Apr. 1996, 97:8, 1989-94.

\* cited by examiner

PRODUCTS CONTAINING POLYPHENOL(S) AND L-ARGININE AND METHODS OF USE THEREOF

This application is a continuation application of U.S. application Ser. No. 09/284,783 filed Apr. 19, 1999, now abandoned, which is a National Stage application of International Application No. PCT/US99/05545, which is a continuation-in-part application of U.S. application Ser. No. 09/041,327 filed Mar. 12, 1998, now abandoned.

FIELD OF THE INVENTION

The invention relates to products containing polyphenols and L-arginine that have a beneficial effect on the health of mammals.

BACKGROUND OF THE INVENTION

Polyphenolic compounds are bioactive substances that are derived from plant materials and are closely associated with the sensory and nutritional quality of products containing them.

Proanthocyanidins are a class of polyphenolic compounds found in several plant species. They are oligomers of flavan-3-ol monomer units most frequently linked either as 4→6 or 4→8. The most common classes are the procyanidins which are chains of catechin, epicatechin, and their gallic acid esters and the prodelphinidins which consist of gallocatechin, epigallocatechin, and their gallic acid esters as the monomeric units. Structural variations in proanthocyanidin oligomers may also occur with the formation of a second interflavanoid bond by C—O oxidative coupling to form A-type oligomers. Due to the complexity of this conversion, A-type proanthocyanidins are not as frequently encountered in nature in comparison to the B-type oligomers.

The term "cocoa polyphenols" includes polyphenolic products including proanthocyanidins, more particularly procyanidins, extracted from cocoa beans and derivatives thereof. More specifically, the term "cocoa polyphenol" includes monomers of the formula $A_n$ (where n is 1) or oligomers of the formula $A_n$ (where n is an integer from 2 to 18, and higher), wherein A has the formula:

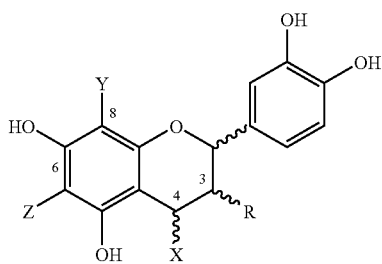

and R is 3-($\alpha$)-OH, 3-($\beta$), 3-($\alpha$)-O-saccharide, 3-($\beta$)-O-saccharide, 3-($\alpha$)-O—C(O)—R', or 3-($\beta$)-O—C(O)—R';

bonding between adjacent monomers takes place at positions 4, 6 or 8;

a bond to a monomer in position 4 has alpha or beta stereochemistry;

X, Y and Z are selected from the group consisting of A, hydrogen, and a saccharide moiety, with the proviso that as to at least one terminal monomer, bonding of the adjacent monomer thereto is at position 4 and optionally Y═Z═hydrogen; and wherein the saccharide moiety is a mono- or di-saccharide moiety and may be optionally substituted with a phenolic moiety and R' may be an aryl or heteroaryl moiety optionally substituted with at least one hydroxyl group; and salts, derivatives and oxidation products thereof.

Preferably, the saccharide moiety is derived from the group consisting of glucose, galactose, xylose, rhamnose and arabinose. The saccharide moiety and any or all of R, X, Y, and Z may optionally be substituted at any position with a phenolic moiety via an ester bond. The phenolic moiety is selected from the group consisting of caffeic, cinnamic, coumaric, ferulic, gallic, hydroxybenzoic and sinapic acids.

Proanthocyanidins have attracted increasing attention due to the rapidly growing body of evidence associating these compounds with a wide range of potential health benefits. Tea catechins have recently been associated with potent antioxidant activity and with the reduction of tumor multiplicity in laboratory mice (Lunder, 1992; Wang et al., 1992; Chung et al., 1992). Additionally, the proanthocyanidins in grape seed extracts have been shown to have free radical scavenging abilities and to decrease the susceptibility of healthy cells to toxic and carcinogenic agents (Bagchi et al., 1997; Waterhouse and Walzem, 1997; Joshi et al., 1998). Polyphenols in grape juice and red wine have been associated with potential cardiovascular benefits, including the reduction of platelet aggregation, modulation of eicosanoid synthesis and inhibition of low-density lipoprotein oxidation (Waterhouse and Walzem, 1997; Schramm et al., 1998; Frankel et al., 1995). Recently, it has been suggested that any potential health benefits attributed to these compounds may be affected by the degree of polymerization (Saito et al. 1998).

Many plant polyphenols have antioxidant activity and have an inhibitory effect on mutagenesis and carcinogenesis. For example, U.S. Pat. Nos. 5,554,645 and 5,712,305 disclose cocoa polyphenol extracts, particularly procyanidins, which have been shown to possess significant biological utility. International_Publication WO 97/36497 (published Dec. 24, 1997) discloses that these extracts also function to reduce periodontal disease, arteriosclerosis and hypertension; inhibit LDL oxidation and DNA topoisomerase II; modulate cyclooxygenase, lipoxygenase, nitric oxide or NO-synthase, apoptosis and platelet aggregation; and possess anti-inflammatory, antigingivitis and antiperiodontis activity. Moreover, WO 97/36497 discloses that polyphenol oligomers 5-12 possess enhanced anti-cancer activity compared to the other polyphenolic compounds isolated from cocoa. Thus, consumption of these higher oligomers in cocoa products may provide significant health benefits.

As previously noted, the use of cocoa extracts or polyphenols derived there from as NO or NO-synthase modulators is described in International Publication WO 97/36497. Nitric oxide has been shown to play a role in many significant biological processes, such as neurotransmission, blood clotting, blood pressure control, regulation of serum lipid levels, cardiovascular disease, cerebral circulation (vascular headache), and a role in the immune system's ability to kill tumor cells and intracellular parasites. P. Clarkson, et al., "Oral L-arginine Improves Endothelium dependent situation in Hypercholesterolemic Young Adults", J. Clin, Innest. 97, No 8: 1989-1994 (April 1996), P. L. Feldman, et al., "The Surprising Life of Nitric Oxide", Chem. & Eng. News, pp. 26-38 (Dec. 20, 1993); S. H. Snyder, et al., "Biological Rules of Nitric Oxide", Scientific American, pp. 68-77 (May 1992); P. Chowienczyk et al., "L-arginine: No More Than A Simple Amino Acid?", Lancet, 350:901-30 (Sep. 27, 1997); M. A. Wheeler, et al., "Efforts of Long Term Oral L-Arginine on The Nitric Oxide Synthase Pathway in The Urine from Patients with Interstitial Cystitis", J. Urology 158:2045-2050 (December 1997); A. Tenenbaum, "L-Arginine: Rediscovery in Progress", Cardiology 90:153-159 (1998); I. K. Mohan, et al., "Effort of L-arginine Nitric Oxide System On Chemical-Induced Diabetes Mellitus", Free Radical Biology & Medicine 25, No. 7: 757-765 (1998); S. Klahr, "The Role of L-Arginine in Hypertension and Nephrotoxicity", Pharmacology and Therapeutics, pp. 547-550 (1998); and R. H. Boger, et al., "Dietary L-arginine and L-Tocopheral Reduce Vascular Oxidation Stress and Preserve Endothelial Function in some Hypocholesteralemic Rabbits via Different Mechanisms," Arterosclerosis 141:31-43 (1998).

For example, health benefits from various foods have been suggested. Peanuts have been reported to be a source of resveratrol, the compound found in grapes and red wine that has been linked to reduced cardiovascular disease. A diet including walnuts has been found to result in reduced serum lipid levels and blood pressure. See Sabate, J. et al., "Effects of Walnuts on Serum Lipid Levels And Blood Pressure in Normal Men", New England J. Med. 328:603-607 (Mar. 4, 1993). It has also been suggested that frequent consumption of nuts may offer protection from coronary heart disease. See Sabate, J. et al., "Nuts: A New Protective Food Against Coronary Heart Disease", Lipidology 5:11-16 (1994). Without wishing to be bound by any theory, a postulated mechanism of action, among others, includes the presence of relatively high levels of arginine in nuts which results in nitric oxide production, thereby causing relaxation of vascular smooth muscle. It is believed that L-arginine is a substrate for nitric oxide production via nitric oxide synthase.

Accordingly, products, such as confectioneries and cocoa-containing products (cocoa powders, chocolate liquors, or extracts thereof) having a high cocoa polyphenol concentration, especially a high concentration of cocoa polyphenol oligomers 5-12 would be desirable. It would also be highly desirable to provide products containing effective amounts of both polyphenols, particularly the cocoa procyanidin(s), and L-arginine to stimulate the production of nitric oxide and elicit the health benefits provided therefrom.

SUMMARY OF THE INVENTION

The invention relates to novel food products comprising at least one polyphenol (i.e., cocoa and/or nut procyanidin) and L-arginine in a combined amount effective to induce a physiological increase in nitric oxide production in a mammal after ingesting the food product. The procyanidin may be synthetic or natural. In a preferred embodiment, the cocoa polyphenol and L-arginine are provided, respectively, by a polyphenol-containing component (e.g., or cocoa and/or cocoa powder and/or nut skin ingredient) and an L-arginine containing component (e.g., a nut meat). However, this invention also encompasses food products in which cocoa and/or nut polyphenol and/or L-arginine is, either of which may be natural or synthetic, added directly to the food product.

The food products of this invention provide health benefits to the mammals ingesting the food products. A particularly advantageous health benefit is the reduction of blood pressure. Other health benefits may include reduced cardiovascular disease, anti-cancer activity, anti-oxidant activity, treatment of renal disease, enhanced immune function, and improved cognitive function.

The cocoa polyphenols contained in the food products of this invention are preferably cocoa polyphenol oligomers 2-18, and more preferably cocoa polyphenol oligomers 5-12.

Cocoa polyphenols, which contain procyanidins, are present in cocoa beans. They are obtained by solvent extraction of powdered unfermented beans as described in U.S. Pat. No. 5,554,645. They are also present in chocolate components prepared from cocoa beans.

Suitable cocoa procyanidin-containing ingredients include roasted cocoa nibs, chocolate liquor, partially defatted cocoa solids, nonfat cocoa solids, cocoa powder milled from the cocoa solids, and mixtures thereof. Preferably, the ingredients are prepared from underfermented beans since these beans contain higher amounts of cocoa polyphenols including the cocoa procyanidins.

One particularly preferred food product of this invention are confectioneries, most preferably chocolates, which include Standard of Identity and Non-Standard of Identity chocolates. The food products of this invention may also be non-chocolate food products. Preferable non-chocolate food products include nut based products such as peanut butter, peanut brittle and the like. Another preferable food product of this invention is a low fat food product prepared with defatted or partially defatted nut meats.

The L-arginine may be derived from any available arginine source, e.g., *Arachis hypogaea* (peanuts), *Juglans regia* (walnuts), *Prunus amygdalus* (almonds), *Corylus avellana* (hazelnuts), *Glycine max* (soy bean) and the like. Also useful are *Carya illinoensis* (pecans), *Amacardium occidentale* (cashews), and *Macadamia integrifolia, M. tetraphylla* (macadamia nuts). It is known that the L-arginine content of nuts can vary according to the nut's maturity and, in addition, certain cultivars may have higher levels. Related species of each genera will also be useful herein. Peanuts generally have about 2-3 g of L-arginine per 100 g of nutmeat. L-arginine content of almonds is about 2-3 g per 100 g, of walnuts about 2-4 g per 100 g, of hazelnuts about 1.5-2.5 g per 100 g, and of pecans and macadamia nuts about 0.5-1.5 g per 100 g. The nut may be nut pieces, a nut skin, a nut paste, and/or a nut flour present in amounts which provide the desired amount of L-arginine, which will vary depending upon the nut source.

The L-arginine-containing ingredient may also be a seed, a seed paste, and/or a seed flour. Suitable seeds include *Helianthus annuus* (sunflower seeds), *Sesamum indicum* (sesame seeds), fenugreek seeds, *Cucurbita* spp.(pumpkins seeds) and the like. Sunflower seeds, pumpkin seeds, and sesame seeds respectively contain about 1.5-3.0 g, about 3.5-6.0 g, and about 2-3 g of L-arginine per 100 g.

Another source high in L-arginine is gelatin which contains about 5 g of L-arginine per 100 g of gelatin.

The food product contains at least about 200 mg, preferably 300 mg, of procyanidins per 100 grams of product and at least about 0.9 g, preferably 1.2 g, more preferably 1.6 g of L-arginine per 100 grams of food product The food product may contain polyphenols from a source other than cocoa, e.g., the polyphenols found in the skins of nuts such as those described above. Peanut skins contain about 17% procyanidins, and almond skins contain up to 30% procyanidins. In a preferred embodiment, the nut skins are used to the food product, e.g., the nougat of a chocolate candy. Polyphenols from fruits and vegetables may also be suitable for use herein. It is known that the skins of fruits such as apples and oranges, as well as grape seeds, are high in polyphenols.

Without being bound to theory, it is believed that the combination of the cocoa polyphenol(s) and L-arginine provides unexpectedly enhanced health benefits because of the positive polyphenol modulation of NO and/or NO-synthase in the presence of L-arginine, a substrate for NO-synthase. Thus, nitric oxide production is increased by the combination of cocoa and/or nut polyphenol and L-arginine which results in improved health benefits derived from nitric oxide, e.g., the prevention of cardiovascular disease, reduced blood pressure, anti-cancer activity, and the like.

This invention is also related to a pharmaceutical composition comprising at least one cocoa and/or nut polyphenol(s), L-arginine, and a pharmaceutically acceptable carrier. The polyphenol(s) and L-arginine are present in a combined amount effective to induce a physiological increase in nitric oxide production in a mammal ingesting the composition. The procyanidin(s) from the cocoa and/or the nut are present in an amount between 1 µg to about 10 g per unit dose. The L-arginine is present in an amount of about 1 µg to about 10 g per unit dose. The cocoa polyphenol ingredient may be an extract of a cocoa material (beans, liquor, or powder, etc.) or may be a synthesized derivative thereof, or may be synthesized polyphenol compound or mixture of polyphenol compounds or derivatives thereof. Procyanidin extracted from nut skins are also suitable for use herein.

DETAILED DESCRIPTION OF THE INVENTION

The food product of this invention contains at least one cocoa polyphenol and optionally polyphenols from other sources as discussed above. The cocoa polyphenol may be from any source, i.e., natural or synthesized. Most preferably, the cocoa polyphenol is an oligomer.

The term "cocoa polyphenol" includes the procyanidins present in cocoa beans or a cocoa ingredients used in the production of chocolate confectioneries, extracts of cocoa beans or a cocoa ingredient comprising procyanidins, and synthesized derivatives thereof, and includes synthesized cocoa polyphenol compounds or synthesized mixtures of cocoa polyphenol compounds, and derivatives thereof. The cocoa beans may be fully fermented or underfermented.

The term "cocoa ingredient" refers to a cocoa solids—containing material derived from shell-free cocoa nibs and includes chocolate liquor, partially or fully defatted cocoa solids (e.g., cake or powder, alkalized cocoa powder, or alkalized chocolate liquor and the like).

The term "chocolate liquor" refers to the dark brown fluid "liquor" formed by grinding a cocoa nib. The fluidity is due to the breakdown of the cell walls and the release of the cocoa butter during the processing resulting in a suspension of ground particles of cocoa solids suspended in cocoa butter.

Partially defatted cocoa solids having a high cocoa polyphenol (CP) content, including a high cocoa procyanidin content, can be obtained by processing the cocoa beans directly to cocoa solids without a bean or nib roasting step. This method conserves the cocoa polyphenols because it omits the traditional roasting step. The method consists essentially of the steps of: a) heating the cocoa beans to an internal bean temperature just sufficient to reduce the moisture content to about 3% by weight and to loosen the cocoa shell; b) winnowing the cocoa nibs from the cocoa shells; c) screw pressing the cocoa nibs; and d) recovering the cocoa butter and partially defatted cocoa solids which contain cocoa polyphenols including cocoa procyanidins. Optionally, the cocoa beans are cleaned prior to the heating step, e.g., in an air fluidized bed density separator. The winnowing can also be carried out in the air fluidized bed density separator. Preferably, the cocoa beans are heated to an internal bean temperature of about 100° C. to about 110° C., more preferably less than about 105° C., typically using a infra red heating apparatus for about 3 to 4 minutes. If desired, the cocoa solids can be alkalized and/or milled to a cocoa powder.

The internal bean temperature (IBT) can be measured by filling an insulated container such as a thermos bottle with beans (approximately 80-100 beans). The insulated container is then appropriately sealed in order to maintain the temperature of the sample therein. A thermometer is inserted into the bean-filled insulated container and the temperature of the thermometer is equilibrated with respect to the beans in the thermos. The temperature reading is the IBT temperature of the beans. IBT can also be considered the equilibrium mass temperature of the beans.

Cocoa beans can be divided into four categories based on their color: predominately brown (fully fermented), purple/brown, purple, and slaty (unfermented). Preferably, the cocoa solids are prepared from underfermented cocoa beans which have a higher cocoa polyphenol content than fermented beans. Underfermented beans include slaty cocoa beans, purple cocoa beans, mixtures of slaty and purple cocoa beans, mixtures of purple and brown cocoa beans, or mixture of slaty, purple, and brown cocoa beans. More preferably, the cocoa beans are slaty and/or purple cocoa beans.

As discussed above, the cocoa polyphenol (CP) content, including the cocoa procyanidin content, of roasted cocoa nibs, chocolate liquor, and partially defatted or nonfat cocoa solids is higher when they are prepared from cocoa beans or blends thereof which are underfermented, i.e., beans having a fermentation factor of 275 or less.

The "fermentation factor" is determined using a grading system for characterizing the fermentation of the cocoa beans. Slaty is designated 1, purple is 2, purple/brown is 3, and brown is 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 [(50×1)+(50×2)].

High CP chocolate liquor and/or high CP cocoa solids can be prepared by: a) roasting the selected cocoa beans (fermentation factor of 275 or less) to an internal bean temperature of 95° C. to 160° C.; b) winnowing the cocoa nibs from the roasted cocoa beans; c) milling the cocoa nibs into the chocolate liquor; and d) optionally recovering cocoa butter and partially defatted cocoa solids from the chocolate liquor. Alternatively, the chocolate liquor and/or cocoa solids can be prepared by: a) heating the selected cocoa beans (fermentation factor of 275 or less) to an internal bean temperature of 95-135° C. to reduce the moisture content to about 3% by weight and to loosen the cocoa shell from the cocoa nibs; b) winnowing the cocoa nibs from the cocoa shells; c) roasting the cocoa nibs to an internal nib temperature of 95° C. to 160° C.; d) milling the roasted nibs into the chocolate liquor; and (e) optionally recovering cocoa butter and partially defatted cocoa solids from the chocolate liquor. Chocolate liquor and partially defatted cocoa solids containing at least 50,000 µg of total cocoa procyanidins and/or at least 5,000 µg of cocoa procyanidin pentamer per gram of nonfat cocoa solids can be prepared by the above processes.

An extract containing cocoa polyphenols including cocoa procyanidins can be prepared by solvent extracting the partially defatted cocoa solids or nonfat cocoa solids prepared from the underfermented cocoa beans or cocoa nibs.

The partially defatted cocoa solids and/or cocoa polyphenol extracts can be used in therapeutic compositions, optionally with a carrier or a diluent. The therapeutic compositions are useful as antineoplastic compositions, antioxidants, antimicrobial agents, nitric oxide (NO) or NO-synthase modulators, cyclo-oxygenase modulators, lipoxygenase modulators, and in vivo glucose modulators.

High CP food products may be prepared using the high CP roasted cocoa nibs, high CP chocolate liquors, and/or high CP partially defatted or nonfat cocoa solids. The food products include pet food, dry cocoa mixes, puddings, syrups, cookies, savory sauces, rice mixes, rice cakes, beverage mixes, beverages and the like. Preferably, the food products are confectioneries, e.g., a dark chocolate or a milk chocolate. The extract can also be used to prepare foods having high cocoa polyphenol contents.

The health of a mammal can be improved by administering to the mammal a composition containing cocoa and/or nut procyanidins or the above high CP cocoa components and/or nut components. In these compositions the total amount of the procyanidin oligomer(s) is at least 1 µg or greater and the composition is administered daily over greater than 60 days.

Cocoa procyanidins may be structurally represented as oligomers of monomer A, having the formula $A_n$, where n is 2-18, where, A has the formula:

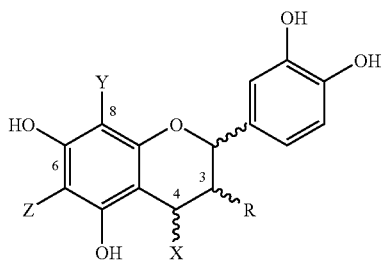

and R is 3-(α)-OH, 3-(β)-OH, 3-(α)-O-saccharide, 3-(β)-O-saccharide; bonding between adjacent monomers takes place at positions 4, 6 or 8; with the proviso that X, Y and Z are selected from the group consisting of A, hydrogen, and a saccharide; a bond to a monomer in position 4 has alpha or beta stereochemistry, as to at least one terminal monomer; and bonding of the adjacent monomer thereto is at position 4. Optionally Y=Z=hydrogen; and salts thereof; wherein the saccharide moiety is derived from a mono- or di-saccharide.

The term "oligomer", as used herein, refers to any compound having the above formula, presented above, wherein n is 2 through 18, and preferably, wherein n is 5-12. When n is 2, the oligomer is termed a "dimer"; when n is 3, the oligomer is termed a "trimer"; when n is 4, the oligomer is termed a "tetramer"; when n is 5, the oligomer is termed a "pentamer"; and similar recitations may be designated for oligomers having n up to and including 18 and higher, such that when n is 18, the oligomer is termed an "octadecamer".

Synthesized derivatives of the cocoa polyphenols include compounds, according to the structure $A_n$, above, wherein R may be 3-(α)-O-saccharide, 3-(β)-O-saccharide, 3-(α)-O—C(O)—$R^1$, or 3-(β)-O—C(O)—$R^1$ wherein the saccharide moiety may be derived from a mono- or di-saccharide selected from the group consisting of glucose, galactose, xylose, rhamnose and arabinose; wherein the saccharide moiety of any or all of R, X, Y, and Z may be optionally substituted at any position with a phenolic moiety via an ester bond; wherein the phenolic moiety may be selected from the group consisting of caffeic, cinnamic, coumaric, ferulic, gallic, hydroxybenzoic and sinapic acids; and wherein $R^1$ is an aryl or heteroaryl moiety optionally substituted with at least one hydroxyl moiety. The substituted aryl or heteroaryl group of $R^1$ may preferably contain a substitution pattern corresponding to the substituted phenolic groups of caffeic, cinnamic, coumaric, ferulic, gallic, hydroxybenzoic or sinapic acids.

The polyphenol oligomers may be prepared by (a) protecting each phenolic hydroxyl group of a first and a second polyphenol monomer with a protecting group to produce a first and second protected polyphenol monomer;

(b) functionalizing the 4-position of the first protected polyphenol monomer to produce a functionalized protected polyphenol monomer having the formula:

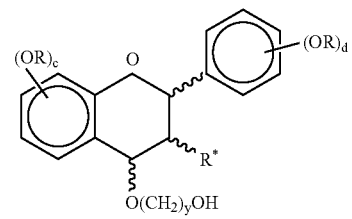

wherein: c is an integer from 1 to 3;
d is an integer from 1 to 4;
y is an integer from 2 to 6;
R is a protecting group; and
R* is H or OH;

(c) coupling the second protected polyphenol monomer with the functionalized protected polyphenol monomer to produce a protected polyphenol dimer as the polyphenol oligomer;

(d) optionally repeating the functionalization and coupling steps to form the polyphenol oligomer having n monomeric units, wherein n is an integer from 3 to 18; preferably 5-12; and (e) removing the protecting groups from the phenolic hydroxyl groups.

The preferred protected polyphenol monomer is a brominated protected epicatechin or brominated protected catechin, more preferably an 8-bromo-epicatechin or an 8-bromo-catechin.

In the above process, the 4-position of the protected polyphenol monomer may be oxidatively functionalized using a quinone oxidizing agent in the presence of a diol, e.g., ethylene glycol when y is 2.

The above process may further comprise the step of forming a derivative of the polyphenol oligomer by esterifying the polyphenol oligomer at the 3-position of at least one monomeric unit to produce an esterified polyphenol oligomer. The ester group may be selected from the group consisting of —OC(O)-aryl, —OC(O)-substituted aryl, —OC(O)-styryl, and OC(O)-substituted styryl, where the substituted aryl or substituted styryl contains at least one substituent selected from the group consisting of halo, hydroxyl, nitro, cyano, amino, thiol, methylenedioxy, dihalomethylenedioxy, a $C_1$-$C_6$ alkyl, a $C_1$-$C_6$ alkoxy, a $C_1$-$C_6$ haloalkyl, a $C_1$-$C_6$ haloalkoxy, a $C_3$-$C_8$ cycloalkyl and a $C_3$-$C_8$ cycloalkoxy. Preferably, the 3-position of at least one monomeric unit is converted to a derivative group derived from an acid selected from the group consisting of caffeic, cinnamic, coumaric, ferulic, gallic, hydroxybenzoic and sinapic acids.

The above process may further comprise the step of forming a derivative of the polyphenol oligomer by glycosylating the polyphenol oligomer at the 3-position of at least one monomeric unit to produce a glycosylated polyphenol oligomer. Preferably, the 3-position of at least one monomeric unit is converted to a derivative group selected from the group consisting of —O— glycoside or an —O-substituted glycoside wherein the substituted glycoside is substituted by —C(O)-aryl, —C(O)-substituted aryl, —C(O)-styryl, or —C(O)-substituted styryl. The substituted aryl or substituted styryl may contain substituents selected from the group consisting of halo, hydroxyl, nitro, cyano, amino, thiol, methylenedioxy, dihalomethylenedioxy, a $C_1$-$C_6$ alkyl, a $C_1$-$C_6$ alkoxy, a $C_1$-$C_6$ haloalkyl, a $C_1$-$C_6$ haloalkoxy, a $C_3$-$C_8$ cycloalkyl and a $C_3$-$C_8$ cycloalkoxy. Preferably, the glycoside is selected from the group consisting of glucose, galactose, xylose, rhamnose, and arabinose.

The food products of this invention may contain one or more of the cocoa polyphenol monomers, oligomers 2-18, or derivatives thereof. Preferably, the food products of this invention contain mixtures of cocoa polyphenol oligomers 2-18, or derivatives thereof; more preferably, the food products contain mixtures of cocoa polyphenol oligomers 5-12, or derivatives thereof.

The food products of this invention include products meant for ingestion by humans and other mammals, e.g. dogs, cats, horses and the like. The food products of this invention can be ingested for nourishment, pleasure, or medical or veterinary purposes.

A preferred food product is a confectionery, a baked product, a condiment, a granola bar, meal replacement bar, a syrup, a powder beverage mix, a beverage, and the like. More preferably, the food product of this invention is a chocolate confectionery containing nuts, e.g., peanuts, walnuts, almonds, hazelnuts, nuts, and the like. The nut meats can be in any form, e.g., whole nuts, chopped nuts, ground nuts, nut pastes, or the like. The preferred non-chocolate food products include peanut butter, peanut brittle and the like. Such non-chocolate food products may contain cocoa ingredients, particularly cocoa polyphenol—containing cocoa ingredients, but would not be considered a chocolate product by one of ordinary skill in the art, e.g., peanut butter containing a relatively small percentage of cocoa powder having high concentrations of cocoa polyphenols.

Chocolate used in foods in the United States is subject to a standard of identity (SOI) established by the U.S. Food and Drug Administration under the Federal Food, Drug and Cosmetic Act that sets out the requisite ingredients, and proportions thereof, of a confection to permit labeling of the confection as a "chocolate."

The most popular chocolate or chocolate candy consumed in the United States is in the form of sweet chocolate or milk chocolate. Chocolate is essentially a mixture of cocoa solids suspended in fat. Milk chocolate is a confection which contains non-fat milk solids, milk fat, chocolate liquor, a nutritive carbohydrate sweetener, cocoa butter and may include a variety of other ingredients such as emulsifying agents, flavorings and other additives. Sweet chocolate contains higher amounts of chocolate liquor, but lower amounts of milk solids than milk chocolate. Semi-sweet chocolate requires at least 35% by weight chocolate liquor and is otherwise similar in definition to sweet chocolate. Dark chocolate generally contains only chocolate liquor, a nutritive carbohydrate sweetener, and cocoa butter, and is by definition either a sweet chocolate or a semi-sweet chocolate. Buttermilk chocolate and skim milk chocolate differ from milk chocolate in that the milk fat comes from various forms of sweet cream, buttermilk, and skim milk, respectively. Skim milk requires the total amount of milk fat to be limited to less than the minimum for milk chocolate. Mixed dairy product chocolates differ from milk chocolate in that the milk solid includes any or all of the milk solids listed for milk chocolate, buttermilk chocolate, or skim milk chocolate. White chocolate differs from milk chocolate in that it contains no non-fat cocoa solids. Heat stable chocolates are also useful herein.

Non-standardized chocolates are those chocolates which have compositions which fall outside the specified ranges of the standardized chocolates. Chocolates are classified as "non-standardized" chocolates when a specified ingredient is replaced, either partially or completely, such as when the cocoa butter is replaced with vegetable oils or fats. Any additions or deletions to a chocolate recipe made outside the US FDA Standards of Identity for chocolate will prohibit use of the term "chocolate" to describe the confectionery. However, as used herein, the term "chocolate" or "chocolate product" refers to any standard of identity or non-standard of identity chocolate product.

Chocolate may take the form of solid pieces of chocolate, such as bars or novelty shapes. Chocolate may also be incorporated as an ingredient in other more complex confections where chocolate is combined with and generally coats other foods inclusions such as caramel, peanut butter, nougat, fruit pieces, nuts, wafers, ice cream or the like. These foods are characterized as microbiologically shelf-stable at 65°-85° F. (18-29° C.) under normal atmospheric conditions.

The term "carbohydrate" refers to nutritive carbohydrate sweeteners, with varying degrees of sweetness intensity and may be any of those typically used and include, but are not limited to, sucrose, (e.g., from cane or beet), dextrose, fructose, lactose, maltose, glucose syrup solids, corn syrup solids, invert sugar, hydrolyzed lactose, honey, maple sugar, brown sugar, molasses and the like.

The chocolate food products may additionally contain other ingredients such as non-fat milk solids, non-fat cocoa solids (cocoa powder), sugar substitutes, natural and artificial flavors (e.g., spices, coffee, salt, etc. as well as mixtures of these), proteins, and the like.

The food products of this invention also include L-arginine. Any L-arginine source may be used, i.e., synthetic or natural. Particularly preferred L-arginine sources include soy beans and nut meats such as peanuts, walnuts, almonds, hazelnuts and the like. Defatted and partially defatted nut meats may also be used to enhance the L-arginine concentration. Partially or fully defatted ground nut meats are referred to as nut flours.

In addition to the physiological activities known to be elicited by cocoa procyanidins or compositions containing cocoa procyanidins, the combination of L-arginine with the cocoa procyanidins produces better effect, as shown by the increased nitric oxide production.

One embodiment of a synergistic effect on NO and/or NO-synthase modulation, for example follows. Many foods contain appreciable amounts of L-arginine, but not necessarily cocoa polyphenols. Given that L-arginine is a substrate for NO-synthase, and NO dependent vasodilatation is significantly improved in hypercholesterolemic animals receiving L-arginine supplementation (See Cooke et al., Circulation 83:1057-1062, 1991) and that cocoa polyphenols can modulate NO levels, a synergistic improvement in endothelium dependent vasodilatation is expected. L-arginine levels of 1.0 to 1.1 g/100 g have been reported in unsweetened cocoa powder. From this basis, other sources of L-arginine are incorporated into the food products to provide for maximal benefit related to NO and NO-synthase modulation. In a particularly preferred embodiment, the cocoa and/or nut polyphenols and L-arginine are present in amounts effective to provide the above described synergistic benefit, e.g., about 1 mg to about 10 g per unit dose, preferably about 25 mg to 3 g of procyanidins. The products of the invention may be used for arresting cancer cell growth in mammals, for reducing hypertension in mammals, treating inflammatory bowel disease, for inhibiting bacterial growth in mammals, for preventing or reducing atherosclerosis or restenosis, for modulating platelet aggregation, for modulating apoptosis, as an antioxidant, specifically for preventing oxidation of LDL in mammals, for modulating cyclo-oxygenase and/or lipoxygenase, for modulating or stimulating nitric oxide (NO) production or nitric oxide (NO) synthase in mammals, for treating nitric oxide (NO) affected hypercholesterolemic in a mammal, for modulating in vivo glucos, for inhibiting tepoisomerase II, for inducing INOS in mammalian monocyte and/or macrophage, as well as an antimicrobial, antineoplastic, anti-gingivitis or anti-periodontitis agent.

Using the food products and pharmaceutical compositions of this invention containing cocoa and/or nut polyphenols and L-arginine, novel methods of improving the health of a mammal, particularly a human, may be practiced.

A preferred embodiment of the invention is a method of improving the health of a mammal by administering an effective amount of the food product or pharmaceutical composition containing cocoa and/or polyphenols and L-arginine to the mammal each day for an effective period of time. Depending on the condition treated, the effective period of time may vary from almost instantaneous to a period greater than sixty days. In one aspect, the mammal's health is improved by ingesting an edible composition containing cocoa polyphenols and L-arginine each day for a period of time greater than five days to a period of time greater than sixty days.

The polyphenols used in this invention modulate nitric oxide (NO) and NO-synthase. The arginine acts as a substrate for NO-synthase. The combined amount of cocoa polyphenol and L-arginine is effective to elicit a physiological response in a mammal receiving the food product. The physiological response is increased in nitric oxide production over that which would be obtained by the administration of the cocoa polyphenol or L-arginine alone. It is believed that this enhanced nitric oxide production results in the aforementioned health benefits associated with nitric oxide production.

The food products and pharmaceutical compositions of this invention are useful, for example, in modulating vasodilation, and are further useful with respect to modulating blood pressure or addressing coronary conditions, and migraine headache conditions. The responses elicited upon administration of the compositions of this invention include lowering hypertension and dilating blood vessels.

The novel food products of this invention can be readily prepared by those of ordinary skill in the art using the teachings set forth herein.

The cocoa ingredients can be prepared from cocoa beans having a fermentation factor of less than 300 and/or from cocoa beans having a fermentation factor of 300 or greater. Alkalized chocolate ingredients prepared from cocoa beans having a fermentation factor of 300 or greater can be used in combination with cocoa ingredients prepared from cocoa beans having fermentation factor of less than 300.

The cocoa procyanidin content of chocolate-based food products can be conserved by protecting the carbohydrate ingredient(s) and/or the milk ingredient(s) during formulation of the food product. The ingredient(s) are protected before adding the chocolate ingredient(s). At least one protective ingredient selected from the group consisting of a fat, an emulsifying agent, an antioxidant, a flavorant, and mixtures thereof is added to the carbohydrate ingredient(s) and/or milk ingredient(s) to form a first mixture. The first mixture is combined with the chocolate ingredient(s) to form a second mixture. The food product is formed from the second mixture.

The food product may be a confectionery or a diet supplement. The confectionery may be a dark or milk chocolate. optionally, the carbohydrate(s) and/or milk ingredient(s) are milled to reduce the particle size prior to mixing with the protective ingredient. The chocolate ingredient(s) may also be milled prior to being combined with the first mixture of protected carbohydrate and/or milk ingredients. Preferred fats for use as pretreatment ingredients are cocoa butter and/or a chocolate liquor which contains cocoa butter and which is prepared from cocoa beans having a fermentation factor of 300 or greater. Preferred emulsifying agents include lecithin and or fractionated lecithin. Suitable antioxidants include tannins, quinones, polyhydroxy compounds, phospholipids, tocol compounds, and/or derivatives thereof. Suitable flavoring agents include vanillin, spices, and/or naturally expressed citrus oils or spice oils. The first mixture, the chocolate ingredient(s), and/or the second mixture can be conched. The chocolate is conched at about 50 to about 65° C. A second emulsifying agent can be added during or after conching. This second emulsifying agent may be lecithin, sucrose polyeruiate, ammonium phosphatide, polyglycerol, polyricinoleate, phosphated mono- and di-glycosides/deactyl tartaric acid esters of monoglycerides, and fractionated lecithin. Food products prepared with the protected carbohydrate(s) and/or milk ingredient(s) contain at least 10 to 20% by weight more cocoa procyanidins than a food product prepared by a process that does not include pretreatment of the carbohydrate ingredient(s) and/or milk ingredient(s).

The addition of L-arginine can be made to the food product by adding an amount of nut meat, e.g., peanuts sufficient to provide fits desired concentration of L-arginine.

As previously noted, a particularly preferred food product is a chocolate confectionery. The chocolate in the chocolate confectionery contains a relatively high concentration of cocoa polyphenols. In this embodiment, the chocolate comprises at least 3,600 μg, preferably at least 4,000 μg, preferably at least 4,500 μg, more preferably at least 5,000 μg, and most preferably at least 5,500 μg cocoa procyanidins per gram of chocolate, based on the total amount of nonfat cocoa solids in the product. According to one preferred embodiment, the chocolate contains at least 6,000 μg, preferably at least 6,500 μg, more preferably at least 7,000 μg, and most preferably at least 8,000 μg of cocoa procyanidins per gram, and even more preferably 10,000 based on the nonfat cocoa solids in the product.

Another embodiment relates to a chocolate food product comprising a chocolate having at least 200 μg, preferably at least 225 μg, more preferably at least 275 μg, and most preferably at least 300 μg cocoa procyanidin pentamer per gram, based on the total amount of nonfat cocoa solids in the chocolate food product. Preferably, the chocolate contains at least 325 μg, preferably at least 350 μg, more preferably at least 400 μg, and most preferably at least 450 μg cocoa procyanidin pentamer per gram, based on the total amount of nonfat cocoa solids in the chocolate food product.

Yet another embodiment, relates to a milk chocolate confectionery which has at least 1,000 μg, preferably at least 1,250 μg, more preferably at least 1,500 μg, and most preferably at least 2,000 μg cocoa polyphenols per gram, based on the total amount of nonfat cocoa solids in the milk chocolate product. In the preferred embodiment, the milk chocolate contains at least 2,500 gg, preferably at least 3,000 μg, more preferably at least 4,000 μg, and most preferably at least 5,000 μg cocoa procyanidins per gram, based on the total amount of nonfat cocoa solids in the milk chocolate product.

In another embodiment, the food product is a milk chocolate which has at least 85 μg, preferably at least 90 μg, more preferably at least 100 µg, and most preferably at least 125 µg cocoa procyanidin pentamer per gram, based on the total amount of nonfat cocoa solids in the milk chocolate product. In a preferred embodiment, the milk chocolate contains at least 150 µg, preferably at least 175 µg, more preferably at least 200 µg, and most preferably at least 250 µg cocoa procyanidin pentamer per gram, based on the total amount of nonfat cocoa solids in the milk chocolate product.

The non-chocolate food products will contain at least 1 µg, preferably at least 5 µg, more preferably at least 10 µg, more preferably at least 25 µg, and most preferably at least 50 µg of cocoa procyanidins. If desired, the non-chocolate food products can contain much higher levels of cocoa procyanidins compared to those found in the above-described chocolate food products.

The amount of L-arginine in the food products can vary. Typically, cocoa contains between 1 to 1.1 grams of L-arginine per 100 grams of partially defatted cocoa solids. It can range from 0.8 to 1.5 per 100 grams of cocoa. The chocolate food products of this invention contain L-arginine in an amount greater than that which naturally occurs in the cocoa ingredients. Knowing the amount of cocoa ingredients and L-arginine used in the food product, one of ordinary skill in the art can readily determine the total amount of L-arginine in the final product.

The food product will generally contain at least 1 µg, preferably at least 10 µg, or at least 100 µg, even more preferably at least 1000 µg, or 5,000 or 10,000 µg, and most preferably at least 20,000, 50,000 or 100,000 µg of L-arginine per gram of food product.

As previously noted, this invention is also directed to a pharmaceutical composition comprising at least one cocoa polyphenol, L-arginine and a pharmaceutically acceptable composition. Inclusion of L-arginine in amounts ranging from about 1 µg to about 10 grams per unit dose may be readily performed by one of ordinary skill in the art. The pharmaceutical compositions of this invention are useful for treating mammals in need of increased nitric oxide production and the benefits that flow therefrom, such as reduced blood pressure.

Test Procedures

The following procedures can be used for quantifying the amount of procyanidins and L-arginine in the various examples.

Method A was used for quantification of the cocoa procyanidin amounts (total and pentamer) reported in Examples 1 to Example 3.

Method B should be used for quantification of the cocoa and nut procyanidin amounts (total and pentamer) in the food products and food ingredients of Examples 4 to 10. Method B was used for quantification of the cocoa procyanidin content of the purified cocoa procyanidin oligomers reported in Example 14 and used in Examples 17-19.

Method C should be used for extracting and identifying nut procyanidins.

Determination of Procyanidin

Method A

Cocoa polyphenol extracts are prepared by grinding a 6-7 g sample using a Tekmar A-10 Analytical Mill for 5 minutes, or, in the case of chocolate liquors, from 6-7 g of chocolate liquor sample without additional grinding. The sample is then transferred to a 50 mL polypropylene centrifuge tube, approximately 35 mL of hexane is added, and sample is shaken vigorously for 1 minute. Sample is spun at 3000 RPM for 10 minutes using an International Equipment Company IECPR-7000 Centrifuge. After decanting the hexane layer, the fat extraction process is repeated two more times. Approximately 1 g of the defatted material is weighed into a 15 mL polypropylene centrifuge tube and 5 mL of a 70% acetone: 29.5% water:0.5% acetic acid solution is added. The sample is vortexed for about 30 seconds using a Scientific Industries Vortex Genie 2 and spun at 300 RPM for 10 minutes in the IECPR-7000 Centrifuge. The liquor is then filtered into a 1 ml hypovial through a Millex-HV 0.45µ filter.

Cocoa polyphenol extracts are analyzed by a Hewlett Packard 1090 Series II HPLC system equipped with a HP model 1046A Programmable Fluorescence detector and Diode Array detector. Separations are effected at 37° C. on a 5µ Supelco Supelcosil LC-Si column (250×4.6 mm) connected to a Supelco Supelguard LC-Si 5 µm guard column (20×2.1 mm). Procyanidins are eluted by linear gradient under the following conditions: (time % A, % B, % C); (0, 82, 14, 4), (30, 67.6, 28.4, 4), (60, 46, 50, 4), (65, 10, 86, 4), followed by a 5 minute re-equilibration. Mobile phase composition is A=dichloromethane, B=methanol, and C=acetic acid:water at a volume ratio of 1:1. A flow rate of 1 mL/min is used. Components are detected by fluorescence, where $\lambda_{ex}$=276 nm and $\lambda_{em}$=316 nm, or by UV at 280 nm. Epicatechin is used as an external standard.

HPLC conditions:
250×4.6 mm Supelco Supelcosil LC-Si column (5 µm)
20×2.1 mm Supelco LC-Si (5 µm)guard column
Detectors: Photodiode Array at 280 nm
Fluorescence $\lambda_{ex}$=276 nm; $\lambda_{em}$=316 nm
Flow rate: 1 mL/min
Column temperature: 37° C.

| Gradient | $CH_2Cl_2$ | Methanol | Acetic Acid Water (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |

Method B

In this method the monomeric and oligomeric cocoa and nut procyanidins are quantitated using a normal-phase high performance liquid chromatography (HPLC) method with fluorescence detection (FLD) instead of UV detection at 280 nm.

The normal-phase HPLC method reported by Hammerstone et al., "Identification of Procyanidins in Cocoa (*Theobroma cacao*) and Chocolate Using High Performance Liquid Chromatography/Mass Spectrometry", J. Agric. Food Chems. 47, 2:490-496(Jan. 14, 1999) was used for the separation and quantification of oligomers up to the decamer.

Procyanidin standards through decamers were obtained by extraction from cocoa beans, enrichment by Sephadex LH-20 gel permeation chromatography, and final purification by preparative normal-phase HPLC. The purity of each oligomeric fraction was assessed using HPLC coupled to mass spectrometry.

A composite standard was then prepared and calibration curves were generated for each oligomeric class using a quadratic fit of area sum versus concentration.

Cocoa beans were provided by the Almirante Center for Cocoa Studies in Itajuipe, Brazil.

The reference compounds are (−)-epicatechin (Sigma Chemical, St. Louis) and purified oligomers from Brazilian cocoa beans.

The cocoa procyanidins are extracted by grinding the fresh seeds in a high-speed laboratory mill with liquid nitrogen until the particle size is reduced to approximately 90 μm. Lipids are removed from 220 g of the ground seeds by extracting three times with 1000 mL of hexane. The lipid-free solids are air dried to yield approximately 100 g of fat free material. A fraction containing procyanidins is obtained by extracting with 1000 mL of 70% by volume acetone in water. The suspension is centrifuged for 10 minutes at 1500×g. The acetone layer is decanted through a funnel with glass wool. The aqueous acetone is then re-extracted with hexane (~75 mL) to remove residual lipids. The hexane layer is discarded and the aqueous acetone is rotary evaporated under partial vacuum at 40° C. to a final volume of 200 mL. The aqueous extract is freeze-dried to yield approximately 19 g of acetone extract material.

For the gel permeation chromatography approximately 2 g of the acetone extract is suspended in 10 mL of 70% aqueous methanol and centrifuged at 1500×g. The supernatant is semi-purified on a Sephadex LH-20 column (70×3 cm) which has previously been equilibrated with methanol at a flow rate of 3.5 mL/min. Two and a half hours after sample loading, fractions are collected every 20 minutes and analyzed by HPLC for theobromine and caffeine (Clapperton et al., "Polyphenols and Cocoa Flavour", Proceedings, 16$^{th}$ International Conference of group Polyphenols, Lisbon, Portugal, Grouppe Polyphenols, Norbonne France, Tome II:112-115 1992). Once the theobromine and caffeine are eluted off the column (~3.5 hours), the remaining eluate is collected for an additional 4.5 hours and rotary evaporated under partial vacuum at 40° C. to remove the organic solvent. Then the extract is suspended in water and freeze-dried.

The cocoa procyanidin oligomers are purified by preparative normal-phase HPLC. Approximately 0.7 g of semi-purified acetone extract is dissolved in 7 mL of acetone:water:acetic acid in a ratio by volume of 70:29.5:0.5, respectively. Separations were effected at ambient temperature using a 5μ Supelcosil LC-Si 100 Å (50×2 cm). Procyanidins were eluted by a linear gradient under the conditions shown in the Table below. Separations of oligomers are monitored by UV at 280 nm and fractions are collected at the valleys between the peaks corresponding to oligomers. Fractions with equal retention times from several preparative separations are combined, rotary evaporated under partial vacuum and freeze-dried.

| | Gradient Profile for Preparative Normal Phase HPLC | | |
|---|---|---|---|
| Time (min) | Methylene Chloride: acetic acid:water (96:2.2 v/v) | Methanol: acetic acid:water (96:2.2 v/v) | Flow rate (mL/min) |
| 0 | 92.5% | 7.5% | 10 |
| 10 | 92.5% | 7.5% | 40 |
| 30 | 91.5% | 8.5% | 40 |
| 145 | 78.0% | 22.0% | 40 |
| 150 | 14.0% | 86.0% | 40 |
| 155 | 14.0% | 86.0% | 50 |
| 180 | 0% | 100% | 50 |

For the mass spectrometry analysis of the partially purified cocoa procyanidin oligomers, purified fractions are analyzed by HPLC/mass spectrometry (MS) using the parameters described by Lazarus et al. "High Performance Liquid Chromatography/mass Spectrometry Analysis of Proanthocyanidins in Food Stuffs", J. Agric. Food Chem. (submitted in 1998). Purities of each fraction are determined by peak area using UV detection at 280 nm in combination with comparing the ratio of ion abundances between each oligomeric class. Composite standard stock solutions are made using commercially available (−)-epicatechin for the monomer and the purified oligomers for dimers through decamers. The oligomeric profile of the composite standard stock solution is shown in the following Table.

| Oligomeric Profile of Composite Standard | |
|---|---|
| Cocoa Procyanidins | Contribution (% by weight) |
| Monomer | 9.82 |
| Dimer | 13.25 |
| Trimer | 9.85 |
| Tetramer | 10.49 |
| Pentamer | 10.51 |
| Hexamer | 12.68 |
| Heptamer | 7.98 |
| Octamer | 8.44 |
| Nonamer | 11.56 |
| Decamer | 5.42 |

Stock solutions are made at the following concentrations: 20 mg/mL, 10 mg/mL, 5 mg/mL, 2 mg/mL, 1 mg/mL and 0.4 mg/mL.

Chocolate liquors and chocolate samples are extracted as above only using (approximately 8 g of sample) 45 mL of hexane. Approximately 1 g of defatted material is extracted as above with 5 mL of acetone:water:acetic acid. The solids are pellitized by centrifuging for 10 mins at 1500×g. Then the supernatant is filtered through a 0.45 nicron nylon filter into an HPLC vial for injection. All defatted samples are weighted, extracted and injected in duplicate. The fat composition of cocoa liquors and chocolates is determined using the AOAC Official Method 920.177. A slight modification to the sample size is needed which incorporates the use of 1 g for the chocolate samples and 0.5 g for the liquor samples. High performance liquid chromatographic analysis of cocoa procyanidins are performed using a HP 1100 Series HPLC (Hewlett Packard, Palo Alto, Calif.) equipped with an auto-injector, quaternary HPLC pump, column heater, fluorescence detector and HP ChemStation for data collection and manipulation. Fluorescence detection is recorded at excitation wavelength 276 nm and emission wavelength 316 nm. Normal phase separations of the procyanidin oligomers are performed using a Phenomenex (Torrance, Calif.) 5μ Lichrosphere silica column (25×4.6 mm) at 37° C. with a 5 μL injection volume. The ternary mobile phase consists of A) dichloromethane, B) methanol and C) acetic acid and water (1:1 v/v). Separations are effected by a series of linear gradients of B into A with a constant 4% C at a flow rate of 1 mL/min as follows: elution starting with 14% B in A; 14-28.4% B in A, 0-30 mins; 28.4-39.2% B in A, 30-45 min; 39.2-86% B in A, 45-50 min. The columns are re-equilibrated between injections with the equivalent of 25 mL (10 column volumes) of the initial mobile phase.

For quantification of cocoa procyanidins in chocolate liquors and chocolates, calibration curves are made from the stock solutions using a quadratic fit for the relationship of area sum versus concentration for the peaks corresponding to each oligomeric class.

Method C

This method is used to determine the type of procyanidins in nuts. Monomeric and oligomeric procyanidins present in nuts are separated by degree of polymerization and identified using a modified normal-phase high performance liquid chromatography (HPLC) method coupled with on-line mass spectrometry (MS) analysis using an atmospheric pressure ionization electrospray (API-ES) chamber. Raw peanuts are provided by M&M/MARS (Hackettstown, N.J.). Raw almonds were provided by the Almond Board of California (Modesto, Calif.).

The standards used are (−)-epicatechin and (+)-catechin. (Sigma Chemical, St. Louis, Mo.).

Solid phase extraction (SPE) columns, (Supelcosil Envi-18 20 mL columns from Supelco, Inc., Bellafonte, Pa.) are rinsed with 3×5 mL of methanol and then conditioned with 3×5 mL of water prior to sample loading. After the appropriate sample loading and rinse procedures, the columns are dried under vacuum for 1-2 min. The SPE column is then soaked in 10 mL of acetone, water and acetic acid in a ratio by volume of 70:29.5:0.5, respectively, for 1 minute before the procyanidins are eluted off the column. To extract the procyanidins from peanut skins, approximately 3.5 g of peanut skins are ground in a laboratory mill before being extracted in 25 mL of acetone, water and acetic acid in a ratio by volume of 70:29.5:0.5, respectively. The suspension is centrifuged for 10 minutes at 1500×g and the supernatant decanted. Twenty milliliters of water is added to the supernatant before the organic solvent is removed by rotary evaporation under partial vacuum at 45° C. to yield approximately 22 mL of aqueous extract. The aqueous extract (22 mL) is loaded onto the pre-conditioned SPE column and rinsed with 40 mL of water. Then the procyanidins are eluted as above. To extract the procyanidins from peanut nutmeat, the nutmeat is frozen in liquid nitrogen and then ground into a powder in a laboratory mill. The nutmeat powder (~10 g) is extracted three times with 45 mL of hexane to remove lipids. One gram of the resultant defatted nutmeat is extracted with 5 mL of acetone, water and acetic acid in a ratio by volume of 70:29.5:0.5, respectively.

With the almond seedcoat, approximately 24 g of seedcoat are removed from the raw almonds using a razor blade. The seedcoat is then defatted twice with 135 mL of hexane and centrifuged for 10 minutes at 1500×g to yield approximately 14.6 g of defatted material. The defatted seedcoat is extracted with 90 mL of acetone, water and acetic acid in a ratio by volume of 70:29.5:0.5, respectively. Thirty milliliters of water are added to the supernatant and the resulting acidified aqueous acetone is rotary evaporated under partial vacuum at 45° C. to a final volume of 50 mL. The aqueous solution is loaded onto the preconditioned SPE column, rinsed with approximately 10 mL of water and the procyanidins eluted as above.

HPLC/MS analyses of the extracts are performed using a HP 1100 Series HPLC as described in Method B above and interfaced to a HP Series 1100 mass selective detector (model G1946A) equipped with an API-ES ionization chamber. The buffering reagent is added via a tee in the eluant stream of the HPLC just prior to the mass spectrometer and delivered with a HP 1100 series HPLC pump bypassing the degasser. Conditions for analysis in the negative ion mode include ~0.75M ammonium hydroxide as the buffering reagent at a flow rate of 0.04 mL/min, a capillary voltage of 3 kV, the fragmentor at 75 V, a nebulizing pressure of 25 psig, and drying gas temperature at 350° C. Data are collected on a HP ChemStation using both scan mode and selected ion monitoring. Spectra are scanned over a mass range of m/z 100-3000 at 1.96 s per cycle.

The mass spectral data of almond seedcoat ions indicates the presence of singly linked procyanidin oligomers through heptamers, whereas the mass spectral data for peanut skins indicates both singly and doubly linked oligomers through octamers. No procyanidins are detected in the peanut meat.

Determination of L-Arginine Content

The L-arginine is determined using the procedure reported in AOAC Official method 982.30, AOAC Official Methods of Analysis 91995), Vitamins and Other Nutrients, Chapter 45, p. 59-61. The sample is acid hydrolyzed and each of 3 hydrolysates is analyzed using parameters optimal for the amino acid analyzer being used. A standard L-arginine solution is used to calibrate the analyzer at least every 24 hours. The nitrogen is determined by AOAC Official Method 955.04C, 920.39A, 976.05 A, or other appropriate Kjidahl method. The uncorrected g/16 g N is computed according to:

g L-arginine (uncorrected 16 g sample N=(n moles L-arginine×Initial sample volume (mL)×MW L-arginine)/(volume sample injected (mL)× sample weight (g)×% N for sample×6.25×10$^5$)

The acid hydrolysis is carried out by placing about 0.1 g (weigh to 0.1 mg accuracy) sample in hydrolysis tube, adding 10 mL 6N Hl, and mixing. The mixture is frozen in a dry ice-alcohol bath. A vacuum of <50 u is drawn and held for 1 minute and the tube was sealed under vacuum. The sample is hydrolyzed for 24 hours at 110+1. The tube is cooled and opened. The hydrolysate is filtered through Whitman No 1 paper. The tube is rinsed three times with water and each rinse is filtered. The filtrate is dried at 65° under vacuum. The dry hydrolysate is dissolved in a volume of buffer appropriate for amino acid analyzer. The hydrolysate can not be stored for greater than one week before using analyzed.

EXAMPLES

The Examples which follow are intended as an illustration of certain preferred embodiments of the invention, and no limitation of the invention is implied. The isolated cocoa procyanidin oligomers used in this Example 17, 18, and 19 were isolated using the procedure described in U.S. Pat. No. 5,554,645 (issued Sep. 10, 1996 to L. Romanczyk et al.) and further purified using the procedure of Method B.

Example 1

Method of Obtaining Cocoa Polyphenol;Cocoa Solids from Cocoa Beans

Commercially available cocoa beans having an initial moisture content of from about 7 to 8 percent by weight were pre-cleaned using an 11"×56" Scalperator (manufactured by Carter Day International, Minneapolis, Minn., USA). Approximately 600 bags of cocoa beans (39,000 kg) were pre-cleaned over a 6.5 hour time period. The beans were fed into the inlet hopper where the flow rate was regulated by a positive feed roll. The beans were fed onto the outside of a rotating wire mesh scalping reel. The beans passed through the wire mesh reel and subsequently through an air aspiration chamber where light dirt, dust and strings were aspirated out of the product stream. The beans that did not pass through the scalping reel were conveyed to the reject stream. This reject stream consisted of large clumps of beans, sticks, stones, etc. The amount of resultant reject was approximately 150 kg, or 0.38% of the starting material. The resulting pre-cleaned product weighed about 38,850 kg and was passed to the bean cleaning step.

The pre-cleaned bean products from the Scalperator were then further cleaned using a Camas International SV4-5 Air Fluidized Bed Density Separator (AFBDS, manufactured by Camas International, Pocotello, Id., USA). About 38,850 kg of cocoa bean products were fed into the AFBDS over a time period of about 6.5 hours. The apparatus removed substantially all heavy impurities such as stones, metal, glass, etc. from the beans, as well as lighter unusable materials such as moldy and infested cocoa beans, resulting in a cleaned bean product which contained substantially only usable cocoa beans. The resulting heavy impurities removed weighed about 50 kg and the light unusable materials weighed about 151 kg. A total of about 38,649 kg of cleaned beans was obtained after both the pre-cleaning and cleaning steps described herein above (99.1% yield after cleaning).

The cleaned cocoa beans were then passed through a infra-red heating apparatus. The apparatus used was the Micro Red 20 electric infra-red vibratory Micronizer (manufactured by Micronizing Company (U.K.) Limited, U.K.). The Micronizer was run at a rate of about 1,701 kilograms per hour. The depth of beans in the vibrating bed of the Micronizer was about 2 inches or about 2-3 beans deep. The surface temperature of the Micronizer was set at about 165° C., resulting in an IBT of about 135° C., for a time ranging from 1 to 1.5 minutes. This treatment caused the shells to dry rapidly and separate from the cocoa nib. Since substantially all of the cocoa beans fed into the Micronizer were whole beans and were substantially free of small broken pieces of bean or shell, no sparks or fires were observed during the infra-red heating step. The broken pieces separated by the vibrating screen prior to the Micronizer were re-introduced into the product stream prior to the winnowing step.

The beans from the Micronizer had a moisture content of about 3.9% by weight. The beans emerged from the Micronizer at an IBT of about 135° C. and were immediately cooled to a temperature of about 90° C. in about three minutes to minimize additional moisture loss. The total beans available after the heating step was about 36,137 kg.

The beans were then subjected to winnowing using a Jupiter Mitra Seita winnower (manufactured by Jupiter Mitra Seita, Jakarta, Indonesia). The winnowing step cracked the beans to loosen the shells and separated the lighter shells from the nibs while at the same time minimizing the amount of nib lost with the shell reject stream. The feed rate into the winnower was about 1,591 kg per hour. The resultant products included about 31,861 kg of usable nibs and 4,276 kg of reject shells. The overall yield of usable nibs from starting material was about 81.7%.

The resulting cocoa nibs were pressed using a Dupps 10-6 Pressor (manufactured by The Dupps Company, Germantown, Ohio, USA). A steady, consistent feed of about 1,402 kg per hour of nibs was fed into two screw presses to extract butter. The press produced about 16,198 kg of cocoa butter which contained about 10% cocoa solids, and about 15,663 kg of cocoa solids which contained about 10% butter.

The cocoa butter was further processed using a Sharples P3000 decanting centrifuge (manufactured by Jenkins Centrifuge Rebuilders, N. Kansas City, Mo., USA). Centrifugation reduced the solids content in the butter to about 1-2% solids and provided about 13,606 kg of butter and 2,592 kg of cocoa solids containing about 40 to 45% butter. The butter containing 1-2% solids was further processed using a plate and frame filter (manufactured by Jupiter Mitra Seita) which removed the remaining solids from the butter and provided about 13,271 kg of clear cocoa butter and about 335 kg of cocoa solids containing 40-45% butter.

The cocoa solids removed from the centrifuge and the filter press contained about 40-45% fat and were pressed in a batch hydraulic press to produce 10% fat cocoa cake. This material produced about 1,186 kg of clear butter and 1,742 kg of cocoa solids.

The total clear butter yield from the incoming beans was 14,456 kg, or 37.1%. The total cocoa solids produced from the incoming beans was 17,405 kg, or 44.6%.

A sample of the partially defatted cocoa solids cocoa powder, produced according to the above-described process from unfermented cocoa beans (fermentation factor 100), contained the following procyanidin concentrations: total procyanidin 32,743 µg/g, procyanidin 9,433 µg/g, procyanidin dimer 5,929 µg/g, procyanidin trimer 5,356 µg/g, procyanidin tramer 4,027 µg/g, procyanidin pentamer 3,168 µg/g, procyanidin hexamer 2,131 µg/g, procyanidin heptamer 1,304 µg/g, procyanidin octamer 739 µg/g, procyanidin nonamer 439 µg/g.

Example 2

Production of Chocolate Liquor Containing Cocoa Polyphenols

Fair average quality (FAQ) Sulawesi cocoa beans having an initial moisture content 7.4% by weight and a fermentation factor level of 233 (31% slaty, 29% purple, 22% purple brown and 17% brown) were selected as the starting material. The cocoa beans were then passed through an infra-red heating apparatus. The apparatus used was an infra-red vibrating micronizer (manufactured by Micronizer Company (U.K.) Limited, U.K.). The feed rate of beans through the infra-red heater and the infra-red heater bed angle were varied to control the amount of heat treatment the beans received. The amount of time the beans spent in the infra-red heater (residence time) was determined by the bed angle and the feed rate. The times used to prepare the materials are listed in the Table 1 below. At the outlet of the micronizer the internal bean temperature (IBT) of the beans was measured, these values are also shown in Table 1.

A 1 kg sample of infra-red heated beans, collected off the infra-red heater at different IBTs, were cracked into smaller pieces. This was done to facilitate the separation of the nib from the shell. The laboratory piece of equipment used to remove the shell was the Limiprimita Cocoa Breaker made by the John Gordon Co. LTD. of England. The cracked beans were next passed through a laboratory scale winnowing system, using a Catador CC-1 manufactured by the John Gordon Co. LTD, England.

The cocoa nibs were next milled into a coarse liquor using a Melange made by Pascall Engineering Co. LTD, England. This device crushes and grinds the nibs into a chocolate liquor. The normal operating temperature for the liquor in the Melange is approximately 50° C. This same process of making nibs to a coarse liquor could be done on a larger production scale using other types of mills, such as a Carle & Montanari Mill. The cocoa nibs were ground in the Melange for one hour. The concentration of cocoa procyanidins was measured for the samples relative to the infra-red heated temperatures. These values are given in the Table 1 below.

TABLE 1

| IBT °C. | Residence Time in Micronizer, (seconds) | Moisture in Finished Liquor (%) | Procyanidin in Defatted Liquor (μg/g) | Total Procyanidins in Defatted Liquor (μg/g) |
|---|---|---|---|---|
| 107 | 42 | 3.9 | 3,098 | 39,690 |
| 126 | 82 | 1.87 | 1,487 | 28,815 |
| 148 | 156 | 1.15 | 695 | 23,937 |

Example 3

Chocolate Food Product

A 10 lb. Sigma blade mixer (manufactured by Teledyne Read Co., York, Pennsylvania) was used to mix together ingredients within the concentration ranges set forth below. The selection of the appropriate ingredients and amounts within the given range to prepare a chocolate is readily performed by one skilled in the art, without undue experimentation.

| Ingredient | % Concentration (by weight) |
|---|---|
| Sucrose | 40% |
| Chocolate Liquor | 7% |
| CP Liquor (Ex. 2) | 49% |
| Fat | 3.5% |
| Lecithin | 0.5% |

The lecithin and fat were combined and mixed, using a 10 lb. Sigma blade mixer until homogeneous. The resulting fat/lecithin mixture was added to the granulated sucrose in a second 10 lb. Sigma mixer. The sucrose, fat and lecithin were mixed at about 35° C. to about 90° C. until homogeneous. The remaining ingredients, including the chocolate liquor of Example 2 having a high concentration of cocoa procyanidins, were added and mixed until homogeneous. The resulting mixture was refined to a micrometer particle size of about 20 microns, conched, standardized. The cocoa procyanidin pentamer concentration of the resulting chocolate ranged from about 385 to 472 μg per gram of chocolate.

Peanuts in an amount of approximately 5-30 percent by weight of the final product are added to form a chocolate-containing peanut product high in cocoa procyanidins and L-arginine.

Example 4

Peanut Butter Food Product

Preroasted peanuts are ground with the addition of salt and sugar as desired to form peanut butter. While mixing, the cocoa powder of Example 1 which has a high cocoa procyanidin content, is added to the mixture in an amount of approximately 2 to 3 percent by weight of the total mixture. The product is a peanut butter containing cocoa polyphenols and L-arginine.

Example 5

Pharmaceutical Composition

A tablet mixture is prepared which comprises the following ingredients (percentages expressed as weight percent):

| Cocoa Powder of Example 1 | 24.0% |
|---|---|
| L-arginine | 5.0% |
| Natural Vanilla Extract | 1.5% |
| Magnesium Stearate (lubricant) | 0.5% |
| Dipac tabletting Sugar | 32.0% |
| Xylitol | 37.0% |

The cocoa powder, vanilla extract and L-arginine are blended together in a food processor for several minutes. The sugars and magnesium stearate are gently mixed together, followed by blending with the cocoa powder/vanilla extract/L-arginine mixture. This material is run through a Manesty Tablet Press (B3B) at maximum pressure and compaction to produce round tablets (15 mm×5 mm) weighing 1.5 to 1.8 grams.

Example 6

Dark Chocolate

A dark chocolate is prepared in a manner substantially similar to the process described in Example 3, using the following general recipe:

| Ingredient Range (wt. %) | |
|---|---|
| 15-35% | Sucrose |
| 40-75% | CP Liquor of Ex. 2 |
| 1-10% | CP Cocoa Powder of Ex. 1 |
| 1-10% | Fat |
| 0.01-0.05% | Vanillin |
| 0.1-1.0% | Lecithin |

Peanuts in an amount of approximately 5 to 30 percent by weight of the total product are added to the dark chocolate.

Example 7

Milk Chocolate

A milk chocolate is prepared in a manner substantially similar to the process described in Example 3, using the following general recipe:

| Ingredient Range (wt. %) | |
|---|---|
| 35-55% | Sucrose |
| 12-25% | Milk Ingredient |
| 10-20% | CP Liquor of (Ex. 2) |
| 15-25% | Fat |
| 0.1-1.0% | Emulsifier |

Almonds in an amount of approximately 5 to 30 percent by weight of the total product are added to the chocolate.

Example 8

| Peanut Butter - Soy Cookie Bar Enrobed with high CP Dark Chocolate | | |
|---|---|---|
| Ingredient | % | Range |
| Dark Chocolate 3.4 mg per g chocolate | 35 | 30-40 |
| Peanuts | 32 | 30-40 |

-continued

Peanut Butter - Soy Cookie Bar
Enrobed with high CP Dark Chocolate

| Ingredient | % | Range |
|---|---|---|
| Soy Flour, low fat | 11 | 10-15 |
| Vegetable Oil | 5 | 2-10 |
| Sugar | 15 | 10-20 |
| Water | 1.5 | |
| Salt | <1 | |
| Caramel Syrup Solution | <1 | |
| Sodium Bicarbonate | <1 | |
| Propyl Gallate | <1 | |

The peanut butter is prepared by combining the peanuts, sugar, vegetable oil, salt and propyl gallate. Cookie is prepared by combining soy flour, water, vegetable oil and sodium bicarbonate, and baking. The peanut butter is then extruded onto the baked cookies and then entire bar is enrobed in the high CP dark chocolate.

Based on the cocoa procyanidin, nut procyanidins, and arginine content of the recipe ingredients, the theoretical procyandin and arginine concentrations are shown below:

| | |
|---|---|
| Total Procyanidins | 120 mg/100 g |
| Arginine | 1.4 g/100 g |

Example 9

Dry Drink Mix Containing High CP Cocoa and L-arginine

A dry drink mix containing the cocoa powder from Example 1 having enhanced levels of cocoa polyphenols (CPs) and L-arginine is made according to the following formulations:

| Ingredient | % |
|---|---|
| Sugar | 59 |
| Skim Milk Powder | 20 |
| Malt Powder | 1.9 |
| CP Cocoa Powder 25-50 mg/g cocoa powder | 8.0 |
| Peanut Flour | 10.0 |
| Vanillin | <0.01 |
| Lecithin | <0.995 |
| Salt | <0.1 |
| Flavoring | <0.1 |

The dry ingredients are batched according to the above formulation and mixed for one hour in a Kitchen Aid Professional Mixer (Model KSM50P) using a wire whip at #2 speed. The lecithin is agglomerated prior to use in the recipe in a Niro-Aeromatic Agglomerator (Model STREA/1).

Based on the cocoa procyanidin, nut procyanidin, and arginine content of the recipe ingredients, the theoretical procyanidin and L-arginine concentrations are shown below:

| | |
|---|---|
| Procyanidins | 200-400 mg/100 g |
| L-arginine | 0.9 g/100 g |

Example 10

| Nut and Seed Bar with Cocoa Extract | |
|---|---|
| Almonds) | 30 |
| Pumpkins Seeds | 12 |
| Sunflower seeds | 5 |
| Sesame seeds | 5 |
| Salt | <1 |
| Butter | 10 |
| Corn syrup | 7.6 |
| Lecithin | <1 |
| Sugar | 26 |
| Cocoa extract | 4 |

Almonds are lightly toasted in salted butter. Pumpkin seeds, sunflower seeds, and sesame seeds are added. Butter, corn syrup, lecithin and salt are combined and heated in microwave oven on ½ power for 1 minute. Sugar is placed in a stainless steel saucepan and cooked on an induction cooker at full power. When the sugar is almost completely melted, heat is reduced to medium power (290° F.) and the sugar cooked until the sugar is fully melted and honey in color. When the sugar is fully melted, it is slowly added to the corn syrup/butter mixture and mixed. The nut mix is placed in a stand mix. The syrup is carefully poured into the nut mix with the paddle on slow speed. The nut/syrup mix is formed into bars and cooled.

Based on the cocoa procyanidin, nut procyanidin, and arginine content of the recipe ingredients, the theoretical procyanidin and arginine concentrations are shown below:

| | |
|---|---|
| Procyanidins | 1586 mg/100 g |
| Arginine | 1.6 g/100 g |

Example 11

| Peanut, Caramel, Nougat, Bar Enrobed in High CP Dark Chocolate | |
|---|---|
| | % Formula |
| CP dark chocolate | 31.5 |
| Peanuts w/skins | 30.0 |
| Caramel | 27.0 |
| Nougat | 11.5 |

A nougat mixture is prepared that contains 45% peanuts and is slabbed onto a cooling table and cut into rectangular bars. A caramel mixture is prepared that contains about 38% peanuts, cooled, and cut into similar pieces. The nougat is topped with the caramel slab and the whole bar is enrobed in chocolate which contains about 10% peanuts.

Based on the cocoa procyanidin, nut procyanidin, and arginine content of the recipe ingredients, the theoretical procyanidin and L-arginine concentration are shown below:

| | |
|---|---|
| Procyanidins | 260 mg/100 g |
| Arginine | 1 g/100 g |

Example 12

Cocoa Source and Method of Preparation

Several *Theobroma cacao* genotypes which represent the three recognized horticultural races of cocoa (Enriquez, 1967; Engels, 1981) were obtained from the three major cocoa-producing regions of the world. A list of those genotypes is shown in Table 2. Other species of Theobroma cacao and its closely related genus Herranina will also be suitable for use herein.

TABLE 2

Description of *Theobroma* cacao Source Material

| GENOTYPE | ORIGIN | HORTICULTURAL RACE |
| --- | --- | --- |
| UIT-1 | Malaysia | Trinitario |
| Unknown | West Africa | Forastero |
| ICS-100 | Brazil | Trinitario (Nicaraguan Criollo ancestor) |
| ICS-39 | Brazil | Trinitario (Nicaraguan Criollo ancestor) |
| UF-613 | Brazil | Trinitario |
| EEG-48 | Brazil | Forastero |
| UF-12 | Brazil | Trinitario |
| NA-33 | Brazil | Forastero |

Harvested cocoa pods were opened and the underfermented beans with the pulp were removed and freeze-dried. The pulp was manually removed. The beans were manually dehulled, and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

Example 12

Procyanidin Extraction Procedures

A. Method 1

Procyanidins were extracted from the defatted, unfermented, 20 freeze-dried cocoa beans of Example 11 using a modification of the method described by Jalal and Collin (1977). Procyanidins were extracted from 50 gram batches of the defatted cocoa mass with 2 400 mL 70% acetone/deionized water followed by 400 mL 70% methanol/deionized water. The extracts were pooled and the solvents were removed by evaporation at 45° C. with a rotary evaporator held under partial vacuum. The resultant aqueous phase was diluted to 1 L with deionized water and extracted 2 times with 400 mL $CHCl_3$. The solvent phase was discarded. The aqueous phase was then extracted 4 times with 500 mL ethyl acetate. Any resultant emulsions were broken by centrifugation on a Sorvall RC 28S centrifuge operated at 2,000×gravity for 30 min. at 10° C. with a rotary evaporator held under partial vacuum. The resultant aqueous phase was frozen in liquid $N_2$, followed by freeze drying on a LABCONCO Freeze Dry System. The yields of crude procyanidins that were obtained from the different cocoa genotypes are listed Table 3.

TABLE 3

Crude Procyanidin Yields

| GENOTYPE | ORIGIN | YIELDS (g) |
| --- | --- | --- |
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

B. Method 2

Alternatively, procyanidins are extracted from the defatted, unfermented, freeze-dried cocoa beans of Example 1 with 70% aqueous acetone. Ten grams of defatted material was slurried with 100 mL solvent for 5-10 min. The slurry was centrifuged for 15 min. at 4° C. at 3000×gravity and the supernatant was passed through glass wool. The filtrate was subjected to distillation under partial vacuum and the resultant aqueous phase was frozen in liquid $N_2$, followed by freeze drying on a LABCONCO Freeze Dry System. The yields of crude procyanidins ranged from 15-20%.

It is believed that the differences in crude yields reflected variations encountered with different genotypes, geographical origin, horticultural race, and method of preparation.

Example 13

Partial Purification of Cocoa Procyanidins

A. Gel Permeation Chromatography

The procyanidins obtained from Example 12 were partially purified by liquid chromatography on Sephadex LH-20 (28× 2.5 cm). Separations were aided by a step gradient from deionized water into methanol. The initial gradient composition started with 15% methanol in deionized water which was followed step wise every 30 min. with 25% methanol in deionized water, 35% methanol in deionized water, 70% methanol in deionized water, and finally 100% methanol. The effluent following the elution of the xanthine alkaloids (caffeine and theobromine) was collected as a single fraction. The fraction yielded a xanthine alkaloid-free subfraction which was submitted to further subfractionation to yield five subfractions designated MM2A through MM2E. The solvent was removed from each subfraction by evaporation at 45° C. with a rotary evaporator held under partial vacuum. The resultant aqueous phase was frozen in liquid $N_2$ and freeze dried overnight on a LABCONCO Freeze Dry System. A representative gel permeation chromatogram showing the fractionation was obtained. Approximately, 100 mg of material was subfractionated in this manner.

Chromatographic Conditions: Column; 28×2.5 cm Sephadex LH-20, Mobile Phase: Methanol/Water Step Gradient, 15:85, 25:75, 35:65, 70:30, 100:0 Stepped at ½ Hour Intervals, Flow Rate; 1.5 mL/min, Detector; UV at $\lambda_1$=254 nm and $\lambda_2$=365 nm, Chart Speed: 9.5 mm/min, Column Load; 120 mg.

B. Semi-preparative High Performance Liquid Chromatography (HPLC)

Method 1. Reverse Phase Separation

Procyanidins obtained from Example 2 and/or 3A were partially purified by semi-preparative HPLC. A Hewlett Packard 1050 HPLC System equipped with a variable wavelength detector, Rheodyne 7010 injection valve with 1 mL injection loop was assembled with a Pharmacia FRAC-100 Fraction Collector. Separations were effected on a Phenomenex Ultracarb™ 10μ ODS column (250×22.5 mm) connected with a Phenomenex 10μ ODS Ultracarb™ (60×10 mm) guard column. The mobile phase composition was A=water; B=methanol used under the following linear gradient conditions; [Time, % A]; (0, 85), (60, 50), (90, 0), and (110, 0) at a flow rate of 5 mL/min. Compounds were detected by UV at 254 nm.

A representative semi-preparative HPLC trace was obtained for the separation of procyanidins present in fraction D+E. Individual peaks or select chromatographic regions were collected on timed intervals or manually by fraction collection for further purification and subsequent evaluation. Injection loads ranged from 25-100 mg of material.

Method 2. Normal Phase Separation

Procyanidin extracts obtained from Examples 2 and/or 3A were partially purified by semi-preparative HPLC. A Hewlett Packard 1050 HPLC system, Millipore-Waters Model 480 LC detector set at 254 nm was assembled with a Pharmacia Frac-100 Fraction Collector set in peak mode. Separations were effected on a Supelco 5 μm Supelcosil LC-Si column (250×10 mm) connected with a Supelco 5 μm Supelguard LC-Si guard column (20×4.6 mm). Procyanidins were eluted by a linear gradient under the following conditions: (Time, % A, % B); (0, 82, 14), (30, 67.6, 28.4), (60, 46, 50, (65, 46, 50), (65, 10, 86), (70, 10, 86) followed by a 10 min. re-equilibra-

| Gradient: Time (min) | $C_2Cl_2$ | Methanol | Acetic Acid: $H_2O$ (1:1) |
|---|---|---|---|
| 0 | 82 | 14 | 4 |
| 30 | 67.6 | 28.4 | 4 |
| 60 | 46 | 50 | 4 |
| 65 | 10 | 86 | 4 |
| 70 | 10 | 86 | 4 |

Example 14

HPLC Purification Methods

Method A. GPC Purification

Procyanidins obtained as in Example 12 were partially purified by liquid chromatography on Sephadex LH 20 (72.5×2.5 cm), using 100% methanol as the eluting solvent, at a flow rate of 3.5 mL/min. Fractions of the eluent were collected after the first 1.5 hours, and the fractions were concentrated by a rotary evaporator, redissolved in water, and freeze-dried. These fractions were referred to as pentamer-enriched fractions. Approximately 2.00 g of the extract obtained from Example 2 was subfractionated in this manner. The results are shown in Table 4.

TABLE 4

| | Composition of Fractions Obtained: | | | | | |
|---|---|---|---|---|---|---|
| Fraction (Time) | Monomer (% Area) | Dimer (% Area) | Trimer (% Area) | Tetramer (% Area) | Pentamer (% Area) | Hexamer (% Area) |
| 1:15 | 73 | 8 | 16 | 3 | ND | ND |
| 1:44 | 67 | 19 | 10 | 3 | 1 | tr |
| 2:13 | 30 | 29 | 24 | 11 | 4 | 1 |
| 2:42 | 2 | 16 | 31 | 28 | 15 | 6 |
| 3:11 | 1 | 12 | 17 | 25 | 22 | 13 |
| 3:40 | tr | 18 | 13 | 18 | 20 | 15 |
| 4:09 | tr | 6 | 8 | 17 | 21 | 19 |
| 1:15 | ND | ND | ND | ND | ND | ND |
| 1:44 | tr | tr | tr | tr | tr | tr |
| 2:13 | 1 | tr | tr | tr | tr | tr |
| 2:42 | 2 | tr | tr | tr | tr | tr |
| 3:11 | 7 | 1 | tr | tr | tr | tr |
| 3:40 | 10 | 2 | 2 | tr | tr | tr |
| 4:09 | 14 | 4 | 4 | 2 | tr | tr |

ND = not detected
tr = trace amount tion. Mobile phase composition was A=dichloromethane; B=methanol; and C=acetic acid:water (1:1). A flow rate of 3 mL/min was used. Components were detected by UV at 254 nm, and recorded on a Kipp & Zonan BD41 recorder. Injection volumes ranged from 100-250 μL of 10 mg of procyanidin extracts dissolved in 0.25 mL 70% aqueous acetone. A representative semi-preparative HPLC trace was obtained. Individual peaks or select chromatographic regions were collected on timed intervals or manually by fraction collection for further purification and subsequent evaluation.

HPLC Conditions: 250×10 mm Supelco Supelcosil LC-si (5 μm) Semipreparative Column
20×4.6 mm Supelco Supelcosil LC-Si (5 μm) Guard Column
Detector: Waters LC Spectrophotometer Model 480 @ 254 nm
Flow rate: 3 mL/min,
Column Temperature: ambient,
Injection: 250 μL of 70% aqueous acetone extract Method B. Normal Phase Separation Procyanidins obtained as Example 12 were separated, purified by normal phase chromatography on Supelcosil LC-Si, 100 Å, 5 μm (250×4.6 mm), at a flow rate of 1.0 mL/min, or, in the alternative, Lichrosphere ° Silica 100, 100 Å, 5 μm (235×3.2 mm), at a flow rate of 0.5 mL/min. Separations were aided by a step gradient under the following conditions: (Time, % A, % B); (0, 82, 14), (30, 67.6 28.4), (60, 46, 50), (65, 10, 86), (70, 10, 86). Mobile phase composition was A=dichloromethane; B=methanol; and C=acetic acid:water (1:1). Components were detected by fluorescence where $\lambda_{ex}$=276 nm and $\lambda_{em}$=316 nm, and by UV at 280 nm. The injection volume was 5.0 μL (20 mg/mL) of the procyanidins obtained from Example 2.

In the alternative, separations were aided by a step gradient under the following conditions: (Time, % A, % B); (0, 76, 20); (25, 46, 50); (30, 10, 86). Mobile phase composition was A=dichloromethane; B=methanol; and C=acetic acid:water (1:1).

Method C. Reverse-Phase Separation

Procyanidins obtained as in Example 12 were separated and purified by reverse phase chromatography on Hewlett Packard Hypersil ODS 5 μm (200×2.1 mm), and a Hewlett Packard Hypersil ODS 5 μm guard column (20×2.1 mm). The procyanidins were eluted with a linear gradient of 20% B into A in 20 minutes, followed by a column wash with 100% B at a flow rate of 9.3 mL/min. The mobile phase composition was a degassed mixture of B=1.0% acetic acid in methanol and A=2.0% acetic acid in nanopure water. Components were detected by UV at 280 nm, and fluorescence where $\lambda_{ex}$=276 nm and $\lambda_{em}$=316 nm; the injection volume was 2.0 μL (20 mg/mL).

Example 15

HPLC Separation of Pentamer Enriched Fractions

Method A. Semi-Preparative Normal Phase HPLC

The pentamer-enriched fractions were further purified by semi-preparative normal phase HPLC by a Hewlett Packard 1050 HPLC system equipped with a Millipore -Waters model 480 LC detector set at 254 nm which was assembled with a Pharmacia Frac-100 Fraction Collector set to peak mode. Separations were effected on a Supelco 5 μm Supelcosel LC-Si, 100 Å column (250×10 mm) connected with a Supelco 5μ Supelguard LC-Si guard column (20×4.6 mm). Procyanidins were eluted by a linear gradient under the following conditions: (Time % A, % B); (0, 82, 14), (30, 67.6, 28.4), (60, 46, 50), (65, 10, 86), (70, 10, 86) followed by a 10 minute re-equilibration. Mobile phase composition was A=dichloromethane; B=methanol; and C=acetic acid:water (1:1). A flow rate of 3 mL/min was used. Components were detected by UV at 254 nm and recorded on a Kipp & Zonan BD41 recorder. Injection volumes ranged from 100-250 μl of 10 mg of procyanidin extracts dissolved in 0.25 mL of 70% aqueous acetone. Individual peaks or select chromatographic regions were collected on timed intervals or manually by fraction collection for further purification and subsequent evaluation.

HPLC conditions: 250×100 mm Supelco Supelcosil LC-Si
(5 μm) Semipreparative Column
20×4.6 mm Supelco Supelcosil LC-Si
(5 μm) Guard Column
Detector: Waters LC
Spectrophotometer Model 480 @ 254 nm
Flow Rates: 3 mL/min.
Column Temperature: ambient
Injection: 250 μL of pentamer enriched extract

| Gradient: | CH$_2$Cl$_2$ | methanol | acetic acid: water (1:1) |
|---|---|---|---|
| 0 | 62 | 14 | 4 |
| 30 | 67.6 | 28.4 | 4 |
| 60 | 46 | 50 | 4 |
| 65 | 10 | 86 | 4 |
| 70 | 10 | 86 | 4 |

Method B. Reverse Phase Separation

Procyanidin extracts obtained as in Example 15 were filtered through a 0.45μ nylon filter and analyzed by a Hewlett Packard 1090 ternary phase HPLC system equipped with a Diode Array detector and a HP model 1046A Programmable Fluorescence Detector. Separations were effected at 45° C. on a Hewlett Packard 5μ Hypersil ODS column (200×2.1 mm). The procyanidins were eluted with a linear gradient of 60% B into A followed by a column wash with B at a flow rate of 0.3 mL/min. The mobile phase composition was a de-gassed mixture of B=0.5% acetic acid in methanol and A=0.5% acetic acid in nanopure water. Acetic acid levels in A and B mobile phases can be increased to 2%. Components were detected by fluorescence, where $\lambda_{ex}$=276 nm and $\lambda_{em}$=316 nm, and by UV at 280 nm. Concentrations of (+)-catechin and (−)-epicatechin were determined relative to reference standard solutions. Procyanidin levels were estimated by using the response factor for (−)-epicatechin.

Method C. Normal Phase Separation

Pentamer-enriched procyanidin extracts obtained as in Example 15 were filtered through a 9.45μ nylon filter and analyzed by a Hewlett Packard 1090 Series II HPLC system equipped with a HP Model 1046A Programmable Fluorescence detector and Diode Array detector. Separations were effected at 37° C. on a 5μ Phenomenex Lichrosphere° Silica 100 column (250×3.2 mm) connected to a Supelco Supelguard LC-Si 5μ guard column (20×4.6 mm). Procyanidins were eluted by linear gradient under the following conditions: (time, % A, % B); (0, 82, 14), (30, 67.6, 28.4), (60, 46, 50), (65, 10, 86), (7, 10, 86), followed by an 8 minute re-equilibration. Mobile phase composition was A=dichloromethane, B=methanol, and C=acetic acid:water at a volume ratio of 1:1. A flow rate of 0.5 mL/min was used. Components were detected by fluorescence, where $\lambda_{ex}$=276 nm and $\lambda_{em}$=316 nm or by UV at 280 nm. A representative HPLC chromatogram showing the separation of the various procyanidins was obtained for one genotype. Similar HPLC profiles were obtained from other Theobroma, Herrania and/or their inter- or intra-specific crosses.

HPLC conditions:

250×3.2 mm henomenex Lichrosphereo° Silica 100
column (5μ) 20×4.6 mm Supelco Supelguard LC-Si (5μ)
guard column
Detectors: Photodiode Array @ 280 nm
Fluorescence $\lambda_{ex}$=276 nm and $\lambda_{em}$=316 nm
Flow rate: 9/5 mL/min.
Column temperature: 37° C.
acetic acid:

| Gradient: | CH$_2$Cl$_2$ | methanol | water (1:1) |
|---|---|---|---|
| 0 | 62 | 14 | 4 |
| 30 | 67.6 | 28.4 | 4 |
| 60 | 46 | 50 | 4 |
| 65 | 10 | 86 | 4 |
| 70 | 10 | 86 | 4 |

Method D. Preparative Normal Phase Separation

The pentamer-enriched fractions obtained as in Example 5 were further purified by preparative normal phase chromatography by modifying the method of Riguad et al., (J. Chrom. 654:255-260. (1993)

Separations were affected at ambient temperature on a 5μ Supelcosil LC-Si 100 Å column (50×2 cm) with an appropriate guard column. Procyanidins were eluted by a linear gradient under the following conditions: (time, % A, % B, flow rate); (0, 92.5, 7.5, 10); (10, 92.5, 7.5, 40); (30, 91.5, 18.5, 40);

(145, 88, 22, 40); (150, 24, 86, 40); (155, 24, 86, 50); (180, 0, 100, 50). Prior to use, the mobile phase components were mixed by the following protocol:

Solvent A preparation (82% $CH_2Cl_2$, 14% methanol, 2% acetic acid, 2% water):
1. Measure 80 mL of water and dispense into a 4 L bottle.
2. Measure 80 mL of water and dispense into the same 4 L bottle.
3. Measure 560 mL of methanol and dispense into the same 4 L bottle.
4. Measure 3280 mL of methylene chloride and dispense into the same 4 L bottle.
5. Cap the bottle and mix well.
6. Purge the mixture with high purity helium for 5-10 minutes to degas.

Repeat steps 1-6 two times to yield 8 volumes of solvent A.

Solvent B preparation (96% methanol, 2% acetic acid, 2% water):
1. Measure 80 mL of water and dispense into a 4 L bottle.
2. Measure 80 mL of acetic acid and dispense into the same 4 L bottle.
3. Measure 3840 mL of methanol and dispense into the same 4 L bottle.
4. Cap the bottle and mix well.
5. Purge the mixture with high purity helium for 5-10 minutes to degas.

Repeat steps 1-5 to yield 4 volumes of solvent B. Mobile phase composition was A=methylene chloride with 2% acetic acid and 2% water; B=methanol with 2% acetic acid and 2% water. The column load was 0.7 g in 7 mL. Components were detected by UV at 254 nm. A typical preparative normal phase HPLC separation of cocoa procyanidins was obtained.

HPLC Conditions:
Column: 50×2 cm 5µ Supercosil LC-Si run @ ambient temperature.
Mobile Phase: A=Methylene Chloride with 2% Acetic Acid and 2% Water.
B=Methanol with 2% Acetic Acid and 2% Water.

| Gradient/Flow Profile | | | |
| --- | --- | --- | --- |
| TIME (MIN) | % A | % B | FLOW RATE (mL/min) |
| 0 | 92.5 | 7.5 | 10 |
| 10 | 92.5 | 7.5 | 40 |
| 30 | 91.5 | 8.5 | 40 |
| 145 | 88.0 | 22.0 | 40 |
| 150 | 24.0 | 86.0 | 40 |
| 155 | 24.0 | 86.0 | 50 |
| 180 | 0 | 100.0 | 50 |

Example 16

Purification of Oligomeric Fractions

Method A. Purification by Semi-Preparative Reverse Phase HPLC

Procyanidins obtained from Example 15, Methods A and B and D, were further separated to obtain experimental quantities of the oligomers. A Hewlett Packard 1050 HPLC system equipped with a variable wavelength detector, Rheodyne 7010 injection valve with 1 mL injection loop was assembled with a pharmacia FRAC-100 Fraction Collector. Separations were effected on a Phenomenex Ultracarb® 10µ ODS column (250×22.5 mm) connected with a Phenomenex 10µ ODS Ultracarb® (60×10 mm) guard column. The mobile phase composition was A=water; B=methanol used under the following linear gradient conditions: (time, % A); (0, 85), (60, 50), (90, 0) and (110, 0) at a flow rate of 5 mL/min. Individual peaks or select chromatographic regions were collected on timed intervals or manually by fraction collection for further evaluation by MADLY-OF/MS and NKr. Injection loads ranged from 25-100 mg of material. A representative elution profile was obtained.

Method B. Modified Semi-Preparative HPLC

Procyanidins obtained from Example 15, Methods A and B and D were further separated to obtain experimental quantities of like oligomers or further structural identification and elucidation (e.g., Example 15, 18, 19, and 20). Supelcosil LC-Si 5µ column (250×10 mm) with a Supelcosil LC-Si 5µ (20×2 mm) guard column. The separations were effected at a flow rate of 3.0 mL/min, at ambient temperature. The mobile phase composition was A=dichloromethane; B=methanol; and C=acetic acid:water (1:1); used under the following linear gradient conditions: (time, % A, % B); (0, 82, 14), (22, 74, 21), (60, 74, 21); (60, 74, 50, 4); (61, 82, 14), followed by column re-equilibration for 7 minutes. Injection volumes were 60 µL containing 12 mg of enriched pentamer. Components were detected by UV at 280 nm. A representative elution profile was obtained.

Example 17

Assessment of Nitric Oxide Synthase Activity

The culture medium used was Medium 200 (Cascade Biologics Inc.) supplemented with Low Serum Growth Supplement (Cascade Biologics Inc.) and 20% fetal calf serum (DAP).

The cocoa procyanidins evaluated were the epicatechin monomer, the dimer, the trimer, the tetramer, the pentamer, and the heptamer. The nitrite content of cocoa procyanidins were evaluated. At the maximal concentration used (100 ⊠ g/ml), no nitrite was detected.

Human umbilical vein endothelial cells (HUVEC) were purchased at primary culture stage from Cascade Biologics Inc. (Portland). Cells were cultured in Medium supplemented with Low Serum Growth Supplement (LSGS) and 20% Fetal Calf Serum (FCS) in 75 $cm^2$ flasks. The cells were seeded for a week following treatment with trypsin-EDTA (2 ml/flask) at 37° C. under 5% $CO_2$ atmosphere. Trypsin was neutralized upon addition of 3 ml. FCS.

The cell suspension was centrifuged for 10 min. at 1200 rpm and the cell pellet was resuspended in the culture medium described above.

Nitric oxide synthase activity was assessed by measuring the nitrite concentration in the culture medium. HUVEC were used between passage 2 to 13. Cells were cultured in 24-well culture plates at the concentration of $5\times10^5$ cells ml in Medium 200 containing LSGS (300 µl per well), and 20% CS. After a 24 hour to 48 hour incubation period at 37° C. under a 5% $CO_2$ atmosphere, the cells were used confluent ($2.5\times10^6$ cells). Medium was removed and fresh was added.

Cocoa procyanidin monomer and oligomers were added to the culture medium at 100 µg/ml, 10 µg/ml or 1 µg/ml (final concentration). Controls consisted of cells cultured without the procyanidins. Reference compounds included acetylcholine, ionomycin (NO synthase stimulator via calcium entry), lipopolysaccharide (NO synthase inductor), and N-methyl L-arginine acetate (inhibitor of NO synthase). The reference compounds were used in order to evidence nitrite production from endothelial NO synthesis.

NO production was estimated by measurement of nitrite ($NO_2$) concentration in culture supernatants according to the Griess reaction. Briefly, 50 µl of conditional medium were incubated with 150 µl of Griess reagent (1% sulfanilamide in 30% acetic acid/0.1% N-(1-naphtyl)-ethylenediamine dihydrochloride in 60% acetic acid) at room temperature for 2 min. The absorbance at 540 nm was determined in a Labsystems MCC/340 multiskan. Nitrite concentration was determined by using sodium nitrite as standard and analyzed using ΔSOFT 2.12 software. The cell-free medium and 100 µg/ml of procyanidins contained no detectable nitrite concentrations.

Raw Data[1]: Showing the Effect of Cocoa Procyanidins On Nitric Oxide Production by HUVEC (13 experiments)

| Treatment | Exp. 1 | Exp. 2 | Exp. 3 | Mean $\bar{X}$ | SD |
|---|---|---|---|---|---|
| Control | 2.6 | 2.9 | 2.4 | 2.6 | 0.3 |
| Acetylcholine $10^{-5}$M | 2.5 | 2.6 | 2.8 | 2.6 | 0.2 |
| Ionomycin 1 µM | 7.8 | 6.3 | 5.4 | 6.5 | 1.2 |
| Ionomycin 1 µM + LNMA 1 µM | 1.8 | 1.9 | 2 | 1.9 | 0.1 |
| LPS 100 mg/ml | 15.6 | 14.3 | 13.2 | 14.4 | 1.2 |
| LPS 100 mg/ml + LNMA 1 µM | 2.2 | 2.3 | 2.6 | 2.4 | 0.2 |
| Monomer | | | | | |
| 1 µg/ml | 2.3 | 2.5 | 2.6 | 2.5 | 0.2 |
| 10 µg/ml | 2.7 | 2.8 | 2.6 | 2.7 | 0.1 |
| 100 µg/ml | 5.4 | 5.9 | 5.7 | 5.7 | 0.3 |
| Dimer | | | | | |
| 1 µg/ml | 2.5 | 2.7 | 2.8 | 2.7 | 0.2 |
| 10 µg/ml | 3.8 | 4.1 | 3.6 | 3.8 | 0.3 |
| 100 µg/ml | 15.1 | 16.4 | 17.2 | 16.2 | 0.1 |
| Trimer | | | | | |
| 1 µg/ml | 3.1 | 3.3 | 3.1 | 3.2 | 0.1 |
| 10 µg/ml | 2.9 | 3.3 | 2.7 | 3.0 | 0.3 |
| 100 µg/ml | 11.5 | 11.8 | 11.9 | 11.7 | 0.2 |
| Tetramer | | | | | |
| 1 µg/ml | 3 | 3.2 | 3.3 | 3.2 | 0.2 |
| 10 µg/ml | 3.6 | 3.7 | 4.1 | 3.8 | 0.3 |
| 100 µg/ml | 8.9 | 9.3 | 9.2 | 9.1 | 0.2 |
| Pentamer | | | | | |
| 1 µg/ml | 1.3 | 1.4 | 1.3 | 1.3 | 0.1 |
| 10 µg/ml | 2.9 | 3.4 | 3 | 3.1 | 0.3 |
| 100 µg/ml | 8.8 | 9.5 | 9.7 | 9.3 | 0.5 |
| Hexamer | | | | | |
| 1 µg/ml | 2.1 | 2.4 | 2.4 | 2.2 | 0.2 |
| 10 µg/ml | 4.8 | 5.6 | 4.3 | 4.9 | 0.7 |
| 100 µg/ml | 9.1 | 10.4 | 9.5 | 9.7 | 0.7 |

[1]Results are expressed as µmol nitrite/$10^6$ cells/48 h

Unstimulated HUVEC produced 2.6±0.3 µM NO over the 48 hour incubation period. Acetylcholine at 10 µM was ineffective in inducing nitric oxide production by HUVEC. In contrast, ionomycin (1 µM) and lipolysaccharide (100 ng/ml) evoked a marked production of nitric oxide. This production of nitric oxide by HUVEC was blocked when N-methyl L-arginine was added to the incubation medium.

The cocoa procyanidin dimer, pentamer, and heptamer evoked a dose-dependent production of NO from HUVEC. Maximum production was observed at the highest concentration tested, i.e., 100 µg/ml. The procyanidin monomer, trimer, and tetramer also evoked a marked production but only at 100 µg/ml concentration. The potency of the various procyanidins, considering the highest dose used is as follows: dimer>trimer>heptamer=pentmer=tetramer>monomer.

Example 18

Nitric Oxide-Dependent Hypertension in the Guinea-Pig

Guinea-pigs (around 400 g body weight, male and female) were anesthetized upon injection of 40 mg/kg sodium pentobarbital. The carotid artery was canulated for monitoring of the arterial blood pressure through a Gould pressure transducer (Model P500). Each of the six cocoa procyanidins, at concentrations of 1, 3, 10, and 25 mg/kg, was injected intravenously through the jugular vein. Alterations in blood pressure were recorded on a polygraph.

In preliminary experiments (2 animals), it was determined that the dose of 100 mg/kg could not be used since the vehicle containing DMSO had a direct effect on mean arterial blood pressure. No marked effect of the vehicle containing DMSO was noted when the dose of 25 mg/kg of the cocoa procyanidin was used (15±5%).

The effects of administering of 1, 3, 10, or 25 mg/kg cocoa procyanidins on arterial blood pressure of anesthetized guinea-pigs was investigated. Upon intravenous injection, the procyanidins monomer and dimer evoked a decrease in blood pressure of about 20%, i.e., not markedly different from injection of solvent alone (15±5%, n=5). In contrast, the cocoa procyanidin trimer, pentamer, and hexamer (10 mg/kg) induced marked decreases in arterial blood pressure, i.e., up to 62-85% for the cocoa procyanidin, tetramer and hexamer. The rank of potency of the various cocoa procyanidins, considering the highest dose used, was as follows: hexamer=tetramer>pentamer>trimer.

TABLE 5

Raw Data: Effect of Cocoa Extracts On The Arterial Blood Pressure of Anesthetized Guinea-Pigs
(6 experiments)

| Procyanidin | Dose mg/kg | Hypertension (%)[1] | | | | | |
| | | Exp 1 | Exp 2 | Exp 3 | Exp 4 | Exp 5 | Exp 6 |
|---|---|---|---|---|---|---|---|
| Monomer | 1 | 55.32 | 70.31 | 70.27 | 75.99 | 71.92 | 77.97 |
| | 3 | 62.99 | 72.62 | 74.59 | 73.33 | 76.04 | 70.44 |
| | 10 | 58.95 | 66.53 | 70.06 | 65.79 | 70.69 | 66.21 |
| | 25 | 46.93 | 55.14 | 63.08 | 53.95 | 65.91 | 58.66 |

TABLE 5-continued

Raw Data: Effect of Cocoa Extracts On The Arterial Blood Pressure of Anesthetized Guinea-Pigs
(6 experiments)

| Procyanidin | Dose mg/kg | Hypertension (%)[1] | | | | | |
|---|---|---|---|---|---|---|---|
| | | Exp 1 | Exp 2 | Exp 3 | Exp 4 | Exp 5 | Exp 6 |
| Dimer | 1 | 74.47 | 90.15 | 92.14 | 89.74 | 96.83 | 94.13 |
| | 3 | 77.64 | 86.29 | 95.29 | 91.74 | 100.6 | 87.08 |
| | 10 | 90.76 | 94.3 | 99.59 | 90.59 | 106.7 | 97.24 |
| | 25 | 88.14 | 95.33 | 106.6 | 88.02 | 110.6 | 94.02 |
| Trimer | 1 | 75.93 | 71.61 | 74.18 | 74.05 | 76.46 | 73.23 |
| | 3 | 94.99 | 100 | 95.05 | 100.7 | 92.47 | 104.8 |
| | 10 | 74.34 | 72.38 | 73.26 | 78.94 | 80 | 70.37 |
| | 25 | 12.27 | 60.42 | 12.31 | 11.6 | 12.23 | 12.56 |
| Tetramer | 1 | 96.86 | 89.19 | 80.31 | 82.47 | 77.64 | 109.9 |
| | 3 | 101.2 | 95.14 | 102.1 | 99.15 | 104.9 | 93.26 |
| | 10 | 96.53 | 0.95 | 7.75 | 12.75 | 7.53 | 102.8 |
| | 25 | 21.7 | 3.45 | 9.61 | 15.21 | 9.07 | 20.83 |
| Pentmer | 1 | 83.41 | 82.57 | 80.81 | 81.57 | 77.55 | 83.05 |
| | 3 | 79.85 | 80.33 | 81.47 | 73.75 | 74.18 | 83.43 |
| | 10 | 87.72 | 83.56 | 82.49 | 75 | 79.81 | 89.35 |
| | 25 | 59.8 | 21.13 | 29.94 | 21.82 | 20.27 | 30.5 |
| Hexamer | 1 | 90.24 | 64.23 | 93.97 | 95.97 | 86.35 | 94.68 |
| | 3 | 74.15 | 81.18 | 83.55 | 80.73 | 69.14 | 71.97 |
| | 10 | 68.8 | 85.41 | 69.49 | 68.04 | 70.85 | 71.47 |
| | 25 | 25.27 | 11.2 | 19.34 | 26.15 | 25.09 | 26.6 |

[1]Results are expressed as % of control mean arterial blood pressure.

A comparison of the in vitro and in vivo results shows the following rank of potency for the cocoa procyanidins:
NO production (100 µg/ml): dimer>trimer>hexamer=pentamer=tetramer>monomer
NO production (10 µg/ml): pentamer, tetramer and dimer (poor induction)
Hypotension: hexamer=tetramer>pentamer>trimer>dimer=monomer.

Except for the dimer, the heptamer or tetramer which induce NO production at the lower dose, were the most effective for inducing drop in arterial blood pressure. These results suggest that cocoa procyanidins can induce in vitro NO production related to an in vivo.

Example 19

Aortic rings from New Zealand white rabbits were set up in 20 ml organ baths. Endothelium dependent relaxation (EDR) to a single dose of ($10^{-5}$ M) cocoa procyanidin and acetylcholine (Ach) were demonstrated in parallel rings pre-contracted with cocoa procyanidins norepinephine (NE) ($10^{-5}$ M). The cocoa procyanidins tested were the monomer, dimer, trimer, tetramer, pentamer, hexamer. Of these, only the pentamer, hexamer, and heptamer demonstrated vasorelaxing activity. Of the two cocoa procyanidin mixtures tested, only the one containing pentamer to decamer (combo 2) showed significant EDR, whereas the other mixture (combo 1) which contained monomer to tetramer had no effect on vascular tone.

Both combo 2 and the pentamer were then used to demonstrate dose dependent vasorelaxation ($10^{-8}$ to $10^{-5}$ M). Rings were incubated for 30' with these cocoa procyanidins ($10^{-5}$ M) and re-tested with Ach and cocoa procyanidins ($10^{-7}$ to $10^{-4}$). Incubation of the tissue with these cocoa procyanadin(s) attenuated EDR evoked by both the cocoa procyanidins and Ach acutely. The maximum relaxation to Ach pre-incubation, 49±5%; post pentamer incubation, 2±1.4%; post combo 2 incubation, 0.8±0.8%: to pentamer pre-incubation, 46.5±4.5%; post incubation, 6.8±3.2%: to combo 2 pre-incubation, 54.3±7%; post incubation, 1.7±1.1%, n=5).

The effect of incubation with both cocoa procyanidins (i.e., abolition of EDR) was restored partially by incubating the tissues with L-arginine ($10^{-4}$ M) for 30' (max relaxation, to Ach: post L-arginine, 21.5±6%; post combo 2, post L-arginine, 13.7±2.6%: to pentamer; post pentamer incubation, post L-arginine, 18.3±5.8%: to combo 2; post combo 2 incubation, post L-arginine, 5.5±2.8%, n=5) The results suggest that depletion of substrate for NO synthase may account for this effect.

The above results are shown in Tables 6 to 9

TABLE 6

Preliminary Experiments On The Effect Of Cocoa Procyanidins On Rabbits Aortic Rings

| | Ach | Monomer | Dimer | Trimer | Tetramer |
|---|---|---|---|---|---|
| % relaxation | 68 | 0 | 0 | 0 | 40 |

| | Pentamer | Hexamer | Heptamer | Monomer-Textramer | Pentamer-Decamer |
|---|---|---|---|---|---|
| % relaxation | 93 | 68 | 47 | 0 | 55 |

TABLE 7

Dose Response Due To Acute Exposure To Cocoa Procyanidins

| Dose (Log mol/l) | $10^{-7}$ | $10^{-6}$ | $10^{-5}$ | $10^{-7}$ | $10^{-6}$ | $10^{-5}$ |
|---|---|---|---|---|---|---|
| | Ach % Relaxation | | | Pentamer % Relaxation | | |
| % Relaxation | 15.2 ± 2.6 | 42.2 ± 4.2 | 49 ± 5.1 | 1.85 ± 0.2 | 8.3 ± 2.5 | 46.5 ± 4.5 |
| | Monomer-Tetramer % Relaxation | | | Pentamer-Decamer % Relaxation | | |
| % Relaxation | Zero | | | 1.4 ± 0.6 | 25.5 ± 8.2 | 54.3 ± 7 |

TABLE 8

Effect Of Incubation With Cocoa Procyanidins and L-arginine

Ach % Relaxation

| Dose (Log mol/l) | $10^{-8}$ | $10^{-7}$ | $10^{-6}$ | $10^{-5}$ |
|---|---|---|---|---|
| Pentamer | 0 | 0 | 2.1 + 1.4 | 0 |
| Pentamer and L-arginine | 0.53 ± 0.5 | 4.5 ± 1.0 | 14.4 ± 5.8 | 21.5 ± 5.7 |

Pentamer % Relaxation

| Dose (Log mol/l) | $10^8$ | $10^{-7}$ | $10^{-6}$ | $10^{-5}$ |
|---|---|---|---|---|
| Pentamer | 0 | 0 | 0 | 6.8 ± 3 |
| Pentamer and L-arginine | 0 | 0.8 ± 0.8 | 5.6 ± 2.5 | 18.3 ± 5.7 |

TABLE 9

| Dose (log mol/l) | $10^{-8}$ | $10^{-7}$ | $10^{-6}$ | $10^{-5}$ |
|---|---|---|---|---|
| Ach % Relaxation | | | | |
| Pentamer-Decamer | 0 | 0.43 ± 0.4 | 0.83 ± 0.8 | 0 |
| Pentamer-Decamer and L-arginine | 3.6 ± 0.8 | 6.4 ± 1.2 | 11.3 ± 2.4 | 13.7 ± 2.6 |
| Pentamer % Relaxation | | | | |
| Pentamer-Decamer | 0 | 0 | 0.58 ± 0.58 | 1.7 ± 1.1 |
| Pentamer-Decamer and L-arginine | 0 | 1.4 ± 1.4 | 3.4 ± 1.9 | 5.5 ± 2.8 |

The above findings demonstrate that only cocoa procyanidins above the trimer are capable of causing vasorelaxation and that cocoa procyanidins have discrete effects on vascular tone which are unlikely to be associated with antioxidant activity.

Other variations and modifications, which will be obvious to those skilled in the art, are within the scope and teachings of this invention. This invention is not to be limited except as set forth in the following claims.

What is claimed is:

1. A non-chocolate food product in a unit dosage form for therapeutic induction of vasorelaxation upon human or veterinary animal consumption comprising:
   (i) cocoa polyphenols in an amount of at least 1 mg/g, and
   (ii) L-arginine in the amount of at least 10 mg/g, with the proviso that when the cocoa polyphenols are provided within a cocoa ingredient, the amount of L-arginine is greater than that provided with the cocoa ingredient;
   wherein the cocoa polyphenols comprise epicatechin, catechin, and procyanidin oligomers 2 to 10, the non-chocolate food product comprises up to 3 g of the cocoa polyphenols per unit dose, and the unit dose is effective to induce endothelium-dependent vasorelaxation in a human or a veterinary animal.

2. The non-chocolate food product of claim 1, wherein the cocoa polyphenols are provided within a cocoa extract.

3. The non-chocolate food product of claim 2, wherein the cocoa polyphenols are present in an amount of at least 3 mg/g.

4. The non-chocolate food product of claim 1, wherein the cocoa polyphenols are provided within a cocoa ingredient.

5. The non-chocolate food product of claim 1, wherein the cocoa polyphenols are present in an amount of at least 1.25 mg/g.

6. The non-chocolate food product of claim 1, wherein the cocoa polyphenols are present in an amount of at least 1.5 mg/g.

7. The non-chocolate food product of claim 1, wherein the cocoa polyphenols are present in an amount of at least 2 mg/g.

8. The non-chocolate food product of claim 1, wherein the cocoa polyphenols are present in an amount of at least 5 mg/g.

9. The non-chocolate food product of claim 1, further comprising at least one ingredient selected from the group consisting of peanuts, walnuts, hazelnuts, almonds, and soy beans.

10. The non-chocolate food product of claim 1, wherein the product is a peanut-based food product.

11. The non-chocolate food product of claim 10, wherein the cocoa polyphenols are present in an amount of at least 3 mg/g.

12. The non-chocolate food product of claim 2, wherein the peanut-based food product is peanut butter.

13. The non-chocolate food product of claim 2, wherein the peanut-based food product is peanut brittle.

14. The non-chocolate food product of claim 1, wherein the food product is a pet food.

15. The non-chocolate food product of claim 14, wherein the cocoa polyphenols are provided within a cocoa extract.

16. The non-chocolate food product of claim 14, wherein the cocoa polyphenols are present in an amount of at least 1.25 mg/g.

17. The non-chocolate food product of claim 14, wherein the cocoa polyphenols are present in an amount of at least 1.5 mg/g.

18. The non-chocolate food product of claim 14, wherein the cocoa polyphenols are present in an amount of at least 2 mg/g.

19. The non-chocolate food product of claim 14, wherein the cocoa polyphenols are present in an amount of at least 5 mg/g.

20. A non-chocolate food product in a unit dosage form for therapeutic induction of vasorelaxation upon human or veterinary animal consumption comprising:
   (i) cocoa polyphenols in the amount of at least 1 mg/g, and
   (ii) L-arginine in the amount of at least 100 mg/g,
   wherein the cocoa polyphenols comprise epicatechin, catechin, and procyanidin oligomers 2 to 10, the non-chocolate food product comprises up to 3 g of the cocoa polyphenols per unit dose, and the unit dose is effective to induce endothelium-dependent vasorelaxation in a human or a veterinary animal.

21. The non-chocolate food product of claim 20, wherein the cocoa polyphenols are present in an amount of at least 1.25 mg/g.

22. The non-chocolate food product of claim 20, wherein the cocoa polyphenols are present in an amount of at least 1.5 mg/g.

23. The non-chocolate food product of claim 20, wherein the cocoa polyphenols are present in an amount of at least 2 mg/g.

24. The non-chocolate food product of claim 20, wherein the cocoa polyphenols are present in an amount of at least 3 mg/g.

25. The non-chocolate food product of claim 20, wherein the cocoa polyphenols are present in an amount of at least 4 mg/g.

26. The non-chocolate food product of claim 20, wherein the cocoa polyphenols are present in an amount of at least 5 mg/g.

* * * * *